(12) United States Patent
Vadurro et al.

(10) Patent No.: US 7,879,108 B2
(45) Date of Patent: Feb. 1, 2011

(54) PROSTHETIC REPAIR FABRIC WITH EROSION RESISTANT EDGE

(75) Inventors: Valerie Vadurro, Warwick, RI (US);
Stephen N. Eldridge, Exeter, RI (US);
Michael J. Lee, Barrington, RI (US);
Roger E. Darois, Foster, RI (US)

(73) Assignee: C. R. Bard, Inc., Murray Hill, NJ (US)

( * ) Notice: Subject to any disclaimer, the term of this patent is extended or adjusted under 35 U.S.C. 154(b) by 1252 days.

(21) Appl. No.: 10/933,080

(22) Filed: Sep. 2, 2004

(65) Prior Publication Data
US 2005/0027369 A1 Feb. 3, 2005

Related U.S. Application Data

(63) Continuation of application No. 10/143,743, filed on May 10, 2002, now Pat. No. 7,011,688.

(51) Int. Cl.
*A61F 2/02* (2006.01)
(52) U.S. Cl. .................................... 623/23.72
(58) Field of Classification Search ... 623/23.72–23.74; 606/213, 215
See application file for complete search history.

(56) References Cited

U.S. PATENT DOCUMENTS

| | | | |
|---|---|---|---|
| 2,671,444 | A | 3/1954 | Pease |
| 3,875,928 | A | 4/1975 | Angelchik |
| 4,271,827 | A | 6/1981 | Angelchik |
| 4,403,604 | A | 9/1983 | Wilkinson et al. |
| 4,769,038 | A | 9/1988 | Bendavid et al. |
| 4,796,603 | A | 1/1989 | Dahlke et al. |
| 4,854,316 | A | 8/1989 | Davis |

(Continued)

FOREIGN PATENT DOCUMENTS

EP 0 719 527 A1 7/1996

(Continued)

OTHER PUBLICATIONS

Basso et al., "360° Laparoscopic Fundoplication With Tension-Free Hiatoplasty in The Treatment of Symptomatic Gastreoesophageal Reflux Disease," 14 *Surg. Endosc.* 164-169 (2000).

(Continued)

*Primary Examiner*—Todd E Manahan
*Assistant Examiner*—Eric Blatt
(74) *Attorney, Agent, or Firm*—Wolf, Greenfield & Sacks, P.C.

(57) ABSTRACT

An implantable prosthesis is provided for repairing or augmenting anatomical weaknesses or defects, and is particularly suitable for the repair of soft tissue and muscle wall openings. The prosthesis may include a repair fabric that is constructed and arranged to allow tissue ingrowth and is susceptible to erosion into and the formation of adhesions with tissue and organs. One or more regions of the prosthesis may be configured to inhibit erosion into and/or the formation of adhesions with tissue and organs. The prosthesis may include an erosion resistant edge to buffer an edge of the fabric from the adjacent tissue or organs. The erosion resistant edge may be provided along an opening that is adapted to receive a tube-like structure, such as the esophagus.

46 Claims, 8 Drawing Sheets

U.S. PATENT DOCUMENTS

| | | |
|---|---|---|
| 5,006,106 A | 4/1991 | Angelchik |
| 5,116,357 A | 5/1992 | Eberbach |
| 5,246,456 A | 9/1993 | Wilkinson |
| 5,258,000 A | 11/1993 | Gianturco |
| 5,290,217 A | 3/1994 | Campos |
| 5,316,543 A | 5/1994 | Eberbach |
| 5,368,602 A | 11/1994 | de la Torre |
| 5,370,650 A | 12/1994 | Tovey et al. |
| 5,397,332 A | 3/1995 | Kammerer et al. |
| 5,433,996 A | 7/1995 | Kranzler et al. |
| 5,456,720 A | 10/1995 | Schultz et al. |
| 5,480,436 A | 1/1996 | Bakker et al. |
| 5,508,036 A | 4/1996 | Bakker et al. |
| 5,593,441 A | 1/1997 | Lichtenstein et al. |
| 5,601,579 A | 2/1997 | Semertzides |
| 5,634,931 A | 6/1997 | Kugel |
| 5,695,525 A | 12/1997 | Mulhauser et al. |
| 5,697,978 A | 12/1997 | Sgro |
| 5,702,416 A | 12/1997 | Kieturakis et al. |
| 5,716,409 A | 2/1998 | Debbas |
| 5,725,577 A | 3/1998 | Saxon |
| 5,743,917 A | 4/1998 | Saxon |
| 5,766,246 A | 6/1998 | Mulhauser et al. |
| 5,769,864 A | 6/1998 | Kugel |
| 5,836,961 A | 11/1998 | Kieturakis et al. |
| 5,840,011 A | 11/1998 | Landgrebe et al. |
| 5,916,225 A | 6/1999 | Kugel |
| 5,919,233 A | 7/1999 | Knopf et al. |
| 5,948,020 A | 9/1999 | Yoon et al. |
| 5,954,767 A | 9/1999 | Pajotin et al. |
| 6,066,777 A | 5/2000 | Benchetrit |
| 6,067,991 A | 5/2000 | Forsell |
| 6,090,116 A | 7/2000 | D'Aversa et al. |
| 6,113,623 A | 9/2000 | Sgro |
| 6,120,539 A | 9/2000 | Eldridge et al. |
| 6,174,320 B1 | 1/2001 | Kugel et al. |
| 6,214,020 B1 | 4/2001 | Mulhauser et al. |
| 6,224,616 B1 | 5/2001 | Kugel |
| 6,258,124 B1 | 7/2001 | Darois et al. |
| 6,270,530 B1 | 8/2001 | Eldridge et al. |
| 6,280,453 B1 | 8/2001 | Kugel et al. |
| 6,287,316 B1 | 9/2001 | Agarwal et al. |
| 6,290,708 B1 | 9/2001 | Kugel et al. |
| 6,319,264 B1 | 11/2001 | Tormala et al. |
| 6,383,201 B1 | 5/2002 | Dong |
| 6,497,650 B1 | 12/2002 | Nicolo |
| 6,638,284 B1 | 10/2003 | Rousseau et al. |
| 6,652,595 B1 | 11/2003 | Nicolo |
| 6,736,823 B2 | 5/2004 | Darois et al. |
| 6,736,854 B2 | 5/2004 | Vadurro et al. |
| 2001/0049539 A1 | 12/2001 | Rehil |
| 2002/0001609 A1 | 1/2002 | Calhoun et al. |
| 2002/0013590 A1 | 1/2002 | Therin et al. |
| 2002/0042658 A1 | 4/2002 | Tyagi |
| 2002/0052654 A1 | 5/2002 | Darois et al. |

FOREIGN PATENT DOCUMENTS

| | | |
|---|---|---|
| EP | 0 898 944 A2 | 3/1999 |
| EP | 0 898 944 A3 | 8/1999 |
| FR | 2 145 975 | 2/1973 |
| FR | 2 744 906 A1 | 8/1997 |
| GB | 1 406 271 | 9/1995 |
| WO | WO 90/14796 | 12/1990 |
| WO | WO 97/35533 | 10/1997 |
| WO | WO 99/56664 | 11/1999 |
| WO | WO 00/07520 A1 | 2/2000 |
| WO | WO 00/42943 | 7/2000 |
| WO | WO 01/06951 A1 | 2/2001 |
| WO | WO 01/08594 A1 | 2/2001 |
| WO | WO 01/54589 A1 | 8/2001 |
| WO | WO 01/81667 A1 | 11/2001 |
| WO | WO 01/85058 A2 | 11/2001 |
| WO | WO 02/22047 A1 | 3/2002 |

OTHER PUBLICATIONS

Carlson et al., "Management of Intrathoracic Stomach With Polypropylene Mesh Prosthesis Reinforced Transabdominal Hiatus Hernia Repair," 187(3) *J. Am. Coll. Surg.* 227-230 (1998).

Carlson et al., "Laparoscopic Prosthetic Reinforcement of Hiatal Herniorrhaphy," 16 *Dig. Surg.* 407-410 (1999).

Carlson et al., "Polypropylene Mesh Reinforced Hiatus Hernia Repair," 112(4) *Gastroentology* (Apr. 1997).

Carugno et al., "Development of an Adjustable Prosthesis For The Treatment of Gastroesophageal Reflux," 44 *ASAIO Journal* 140-143 (1998).

Champion et al., "Laparoscopic Mesh Cruroplasty for Large Paraeosphageal Hernias," *Surgical Endoscopy and Other Interventional Techniques*, Feb. 17, 2003, pp. 551-553, vol. 17, No. 4.

Edelman, David S., M.D., "Laparoscopic Paraesophageal Hernia Repair with Mesh", *Surgical Laparoscopy & Endoscopy*, 1995, pp. 32-37, vol. 5, No. 1.

Frantzides et al., "Laparoscopic Repair of Large Hiatal Hernia With Polytetrafluoroethylene," 13 *Surg. Endosc.* 906-908 (1999).

Frantzides et al., "Prosthetic Reinforcement of Posterior Cruroplasty During Laparoscopic Hiatal Herniorrhaphy," 11 *Surg. Endosc.* 769-771 (1997).

Gryska, P. M.D., "Tension Free Repair of Hiatal hernia During Laparoscopic Fundoplication," poster submission to New England Surgical Society 82d Annual Meeting, Sep. 21-23, 2001, providence, Rhode Island.

Gryska, P. M.D., "Tension-Free Repair of Hiatal Hernia During Laparoscopic Fundoplication," American College of Surgeons Scientific Exhibition of the 87th Clinical Congress, Oct. 7-12, 2001, New Orleans, Louisiana.

Huntington, "The Surgeon at Work: Laparoscopic Mesh Repair of The Esophageal Hiatus," 184 *J. Am. Coll. Surg.* 399-400 (Apr. 1997).

Kennedy, "Hiatus Hernia Repair Clinical and Radiological Results of a New Combined Thoracoabdominal Technique," 1 *Med. J. Australia* 386-390 (1974).

Kozarek et al., "Evaluation of Angelchik Antireflux Prosthesis: Long Term Results", 30(8) *Digestive Diseases and Sciences* 723-732 (Aug. 1985).

Lees et al., "Esophageal Perforation: A Complication of The Angelchik Prosthesis," 50(4) *Cleve. Clin. Q.* 449-451 (1983).

Patel et al., "Angelchik Antireflux Prosthesis—Its Usefulness and Review of Literature," 79(1) *Am. J. of Gastroenterology* 12-15 (1984).

Paul, et al., "Laparoscopic tension-free repair of large paraesophageal hernias", *Surg Endosc.*, 1997, pp. 303-307, vol. 11.

Sakashita et al., "Repair of Posttraumatic and Recurrent Diaphragm Hernias With Prosthetic Mesh," 15(1) *Acta Medica et Biologica* 1-14 (1967).

Simpson et al., "Prosthetic Patch Stabilization of Crural Repair in Antireflux Surgery in Children," *The American Surgeon*, Jan. 1998, pp. 67-69, vol. 64.

Thibault et al., "The Angelchik Antireflux Prosthesis: Long-Term Clinical and Technical Follow-up," 37(1) *Canadian J. Surg.* 12-17 (Feb. 1994).

Waldhausen et al., "The Diagnosis and Management of Traumatic Injuries of the Diaphragm Including The Use of Marlex Prostheses," 6(3) *J. of Trauma* 332-343 (1966).

Watanabe et al., "Laparoscopic Repair of a Paraesophageal Hiatus Hernia Without Fundoplication," 27 *Surgery Today* 1093-1096 (1997).

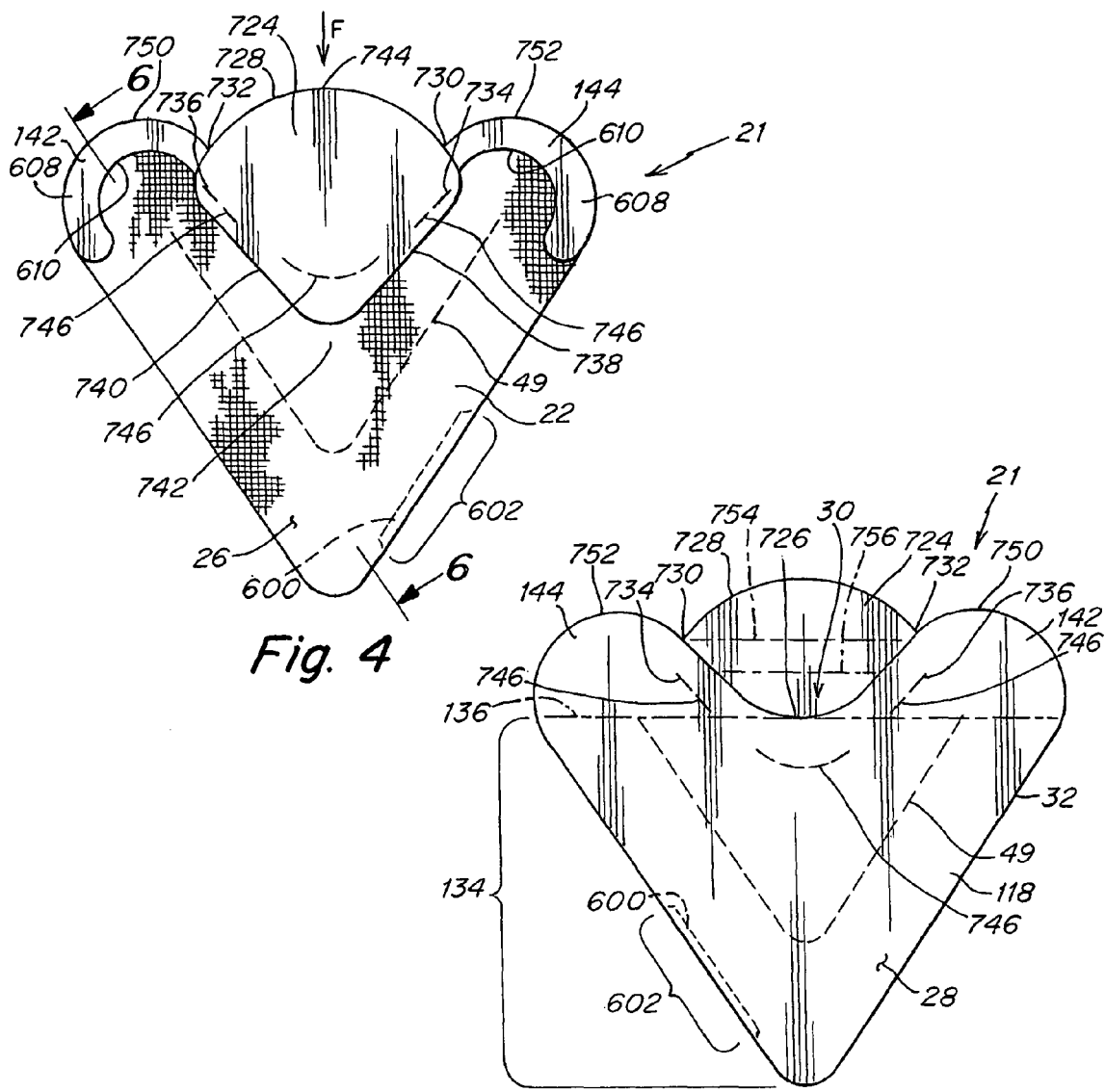
Fig. 4
Fig. 5
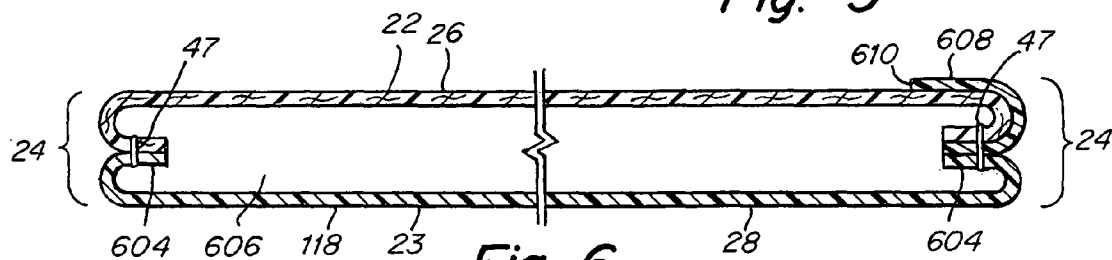
Fig. 6
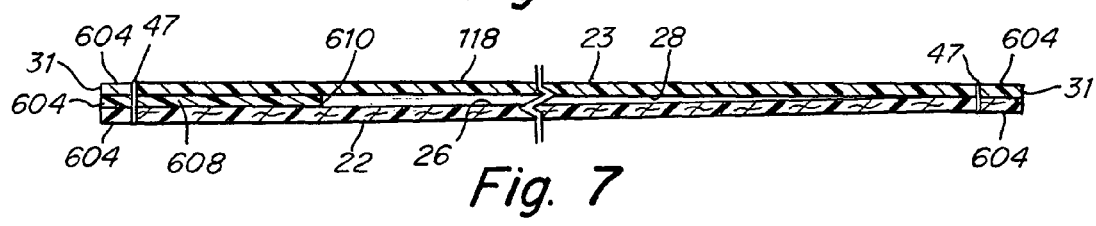
Fig. 7

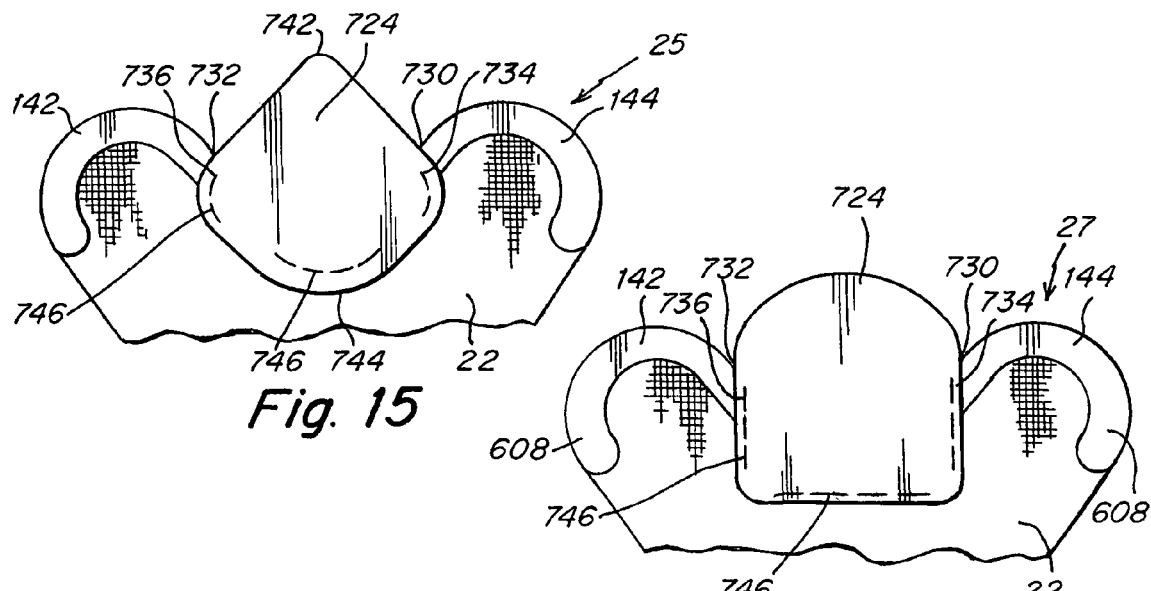
Fig. 15
Fig. 16
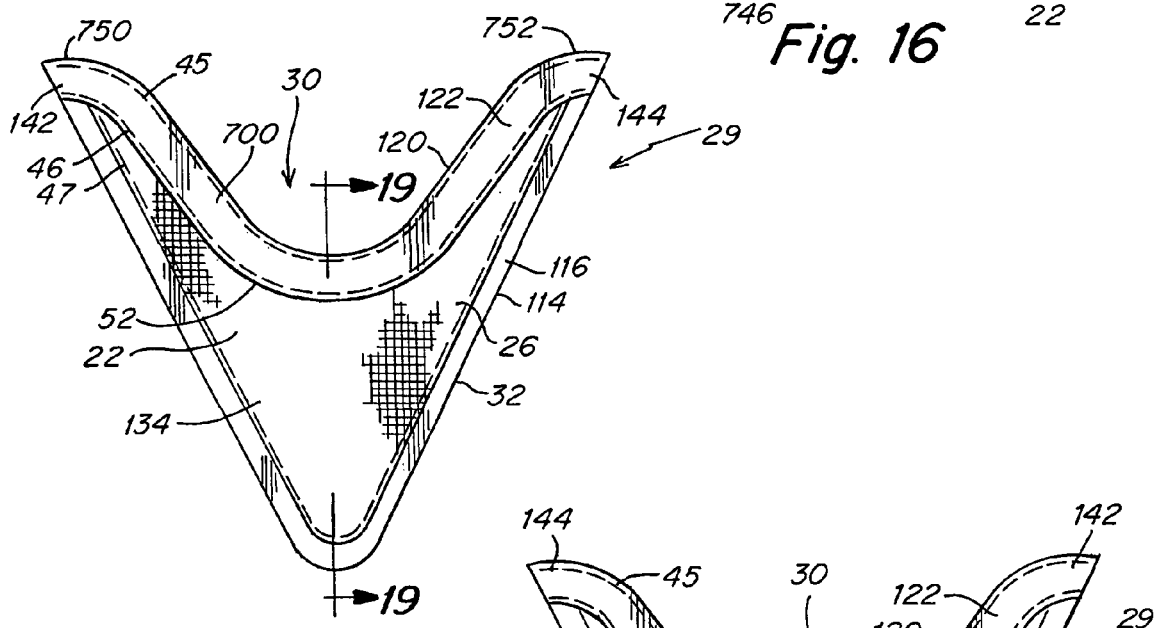
Fig. 17
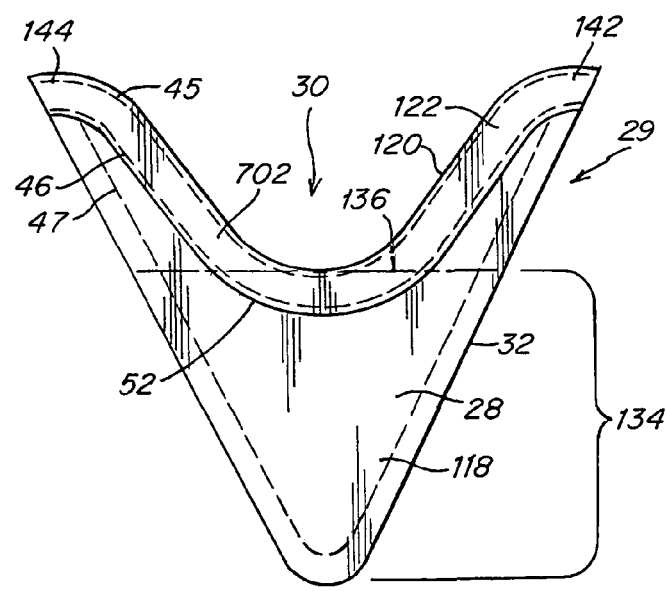
Fig. 18

PROSTHETIC REPAIR FABRIC WITH EROSION RESISTANT EDGE

This application is a continuation of U.S. application Ser. No. 10/143,743, filed on May 10, 2002.

FIELD OF THE INVENTION

The present invention relates to an implantable prosthesis, and more particularly to a prosthetic repair fabric for use in soft tissue repair and reconstruction.

DISCUSSION OF RELATED ART

Various prosthetic repair materials have been proposed to repair and reinforce anatomical defects, such as tissue and muscle wall hernias. For example, a hiatal hernia occurs when a natural opening, or "hiatus," in the diaphragm through which the esophagus extends, becomes enlarged, allowing the stomach to pass through the hiatus into the thoracic cavity.

Representative surgical treatments for a hiatal hernia may include a cruroplasty, which involves tightening the crura of the diaphragm around the esophagus to reduce the size of the hiatal hernia. It has also been known to use a prosthetic repair fabric in the surgical treatment of a hiatal hernia. Typically, a sheet of surgical mesh fabric, such as BARD MESH, commercially available in rectangular stock sheets, was custom fashioned by a surgeon into a shape suitable for a particular patient's hiatal repair, such as a rectangular or oval shape. Typically, the surgeon placed the mesh implant over the hiatal hernia.

It is one object of certain embodiments of the present invention to provide a preformed prosthesis for the repair of a hiatal hernia.

It is another object of certain embodiments of the present invention to provide a prosthesis for the repair of tissue defects, such as a hiatal hernia, that reduces the incidence of postoperative adhesions to and or erosion of tissue and organs, such as the esophagus, stomach and/or other surrounding viscera.

SUMMARY OF THE INVENTION

In one illustrative embodiment of the invention, an implantable prosthesis is provided for repairing a tissue or muscle wall defect. The implantable prosthesis comprises a repair fabric that is susceptible to erosion into and the formation of adhesions with tissue and organs, and an edge barrier that inhibits erosion into tissue and organs and inhibits the formation of adhesions with tissue and organs. The repair fabric includes first and second surfaces and a fabric edge extending from the first surface to the second surface. The first surface is adapted to face the tissue or muscle wall defect and the second surface is adapted to face away from the defect. The edge barrier is disposed on a portion of the first and second surfaces adjacent the fabric edge and extends from the first surface to the second surface over the fabric edge. The edge barrier has an inner surface that is spaced from the fabric edge in a direction normal to the fabric edge to form a gap between the inner face of the edge barrier and the fabric edge to inhibit erosion of the tissue and organs by the fabric edge and to inhibit the formation of adhesions to the fabric edge.

In another illustrative embodiment of the invention, an implantable prosthesis is provided for repairing a tissue or muscle wall defect. The implantable prosthesis comprises a repair fabric that is susceptible to the formation of adhesions with and erosion into tissue and organs, and an edge barrier that inhibits erosion into tissue and organs and inhibits the formation of adhesions. The repair fabric includes first and second surfaces and a fabric edge extending from the first surface to the second surface. The first surface is adapted to face the muscle or tissue wall defect and the second surface is adapted to face away from the defect. The edge barrier is disposed at all times over the fabric edge. The edge barrier has an inner surface that is spaced from the fabric edge in a direction normal to fabric edge to form a gap between the inner face of the edge barrier and the fabric edge to inhibit erosion of the tissue and organs by the fabric edge and to inhibit the formation of adhesions to the fabric edge.

In a further illustrative embodiment of the invention, an implantable prosthesis is provided for repairing a tissue or muscle wall defect in the vicinity of a tube-like structure. The implantable prosthesis comprises a repair fabric of implantable, biologically compatible material. The repair fabric has an opening that is adapted to receive the tube-like structure. The repair fabric includes a body portion and first and second tails extending away from the body portion. The body portion is configured in a generally triangular shape with a base having first and second segments. The first tail extends from the first segment of the base and the second tail extends from the second segment of the base. The opening is located along the base between the first and second tails.

In yet another illustrative embodiment of the invention, an implantable prosthesis is provided for repairing a tissue or muscle wall defect in the vicinity of a tube-like structure. The implantable prosthesis comprises a repair fabric of implantable, biologically compatible material. The repair fabric has a generally heart shaped outer periphery with an opening along a portion of the outer periphery that is adapted to receive the tube-like structure.

In yet a further illustrative embodiment of the invention, a prosthetic repair fabric is provided for repairing a tissue or muscle wall defect in the vicinity of a tube-like structure. The prosthetic repair fabric comprises a layer of fabric that is susceptible to the formation of adhesions with and erosion into tissue and organs, and an edge barrier that is adapted to inhibit the formation of adhesions with an edge of the fabric. The layer of fabric has an opening that is adapted to receive the tube-like structure. The repair fabric includes a body portion and first and second tails extending away from the body portion with the opening being located along the edge of the fabric between the first and second tails. The edge barrier is attached to the first tail at a first attachment point and to the second tail a second attachment point. The first and second attachment points are aligned with each other across a segment of the opening. A portion of the edge barrier overlies a portion of the opening and extends between the first and second attachment points.

Other objects and features of the present invention will become apparent from the following detailed description when taken in connection with the accompanying drawings. It is to be understood that the drawings are designed for the purpose of illustration only and are not intended as a definition of the limits of the invention.

BRIEF DESCRIPTION OF THE DRAWINGS

The foregoing and other objects and advantages of the invention will be appreciated more fully from the following drawings, wherein like reference characters designate like features, in which:

FIG. 4 is a top plan view of a prosthetic repair fabric in accordance with another illustrative embodiment of the present invention;

FIG. 5 is a bottom plan view of the prosthetic repair fabric of FIG. 4;

FIG. 6 is a cross-section view of the prosthetic repair fabric of FIG. 4 taken along section line 6-6;

FIG. 7 is a cross-sectional view of the prosthetic repair fabric similar to FIG. 6 before inversion of the prosthesis;

FIG. 15 is a partial top plan view of a prosthetic repair fabric in accordance with another illustrative embodiment of the invention;

FIG. 16 is a partial top plan view of a prosthetic repair fabric in accordance with a further illustrative embodiment of the invention;

FIG. 17 is a top plan view of a prosthetic repair fabric in accordance with another illustrative embodiment of the present invention;

FIG. 18 is a bottom plan view of the prosthetic repair fabric of FIG. 17;

DESCRIPTION OF ILLUSTRATIVE EMBODIMENTS

Figure 1:
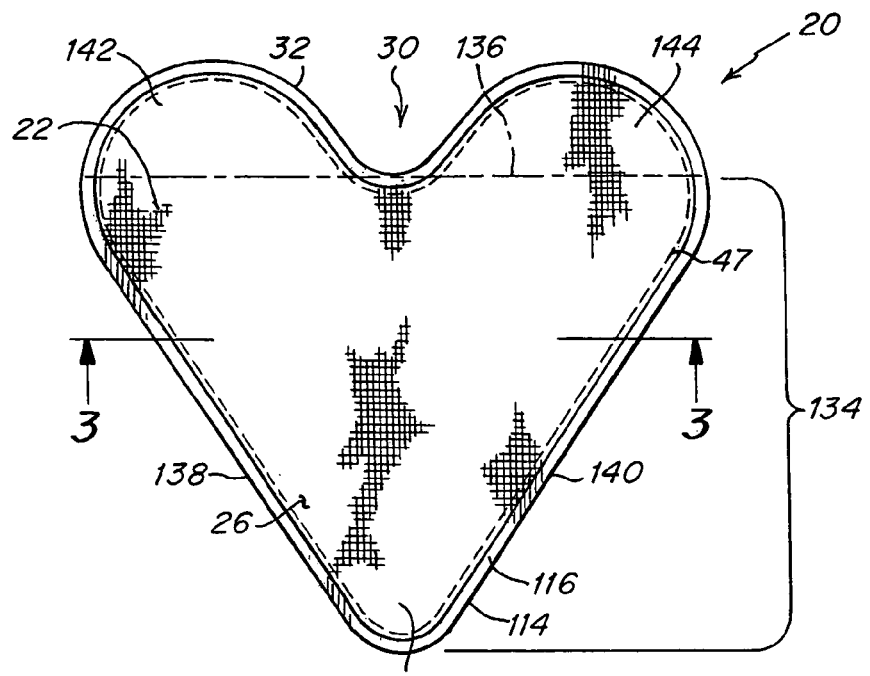
FIG. 1 is a top plan view of a prosthetic repair fabric in accordance with an illustrative embodiment of the present invention.

The invention is directed to an implantable prosthesis for repairing or augmenting anatomical weaknesses or defects, and is particularly suitable for the repair of soft tissue and muscle wall openings. For ease of understanding, and without limiting the scope of the invention, the prosthesis to which this patent is addressed is described below particularly in connection with a hiatal hernia repair. It should be understood, however, that the prosthesis is not so limited and may be employed in other anatomical procedures, as would be apparent to one of skill in the art. For example, the prosthesis may be used where a tube-like structure or other projection extends from or passes through an opening in a tissue muscle or organ wall requiring repair and/or augmentation.

The prosthesis may be configured to reduce the incidence of post-operative erosion into adjacent tissue or organs, such as the esophagus or other cord-like structure, that may come into contact with the prosthesis. Tissue and organs may be particularly susceptible to erosion or abrasion by the edge of a prosthetic repair fabric that is positioned proximate to tissue and organs which lie transverse to the plane of the prosthetic fabric material, particularly in dynamic environments, such as the diaphragm. Thus, the prosthesis may be provided with one or more erosion-resistant edges that act to buffer or otherwise isolate the edge of the repair fabric so as to reduce the incidence of erosion into adjacent tissue or organs.

A prosthesis with erosion resistant characteristics may be particularly suitable in the repair of a hiatal hernia. The esophagus presents a projecting structure proximate and generally perpendicular to the plane of the defect in the diaphragm. The diaphragm moves to assist in breathing with sudden and extreme movement occurring in the case of coughing or sneezing, while the esophagus moves to assist in swallowing and regurgitating. This very dynamic environment of the esophagus and diaphragm may increase potential erosion of the esophagus by a prosthesis implanted to repair the defect.

Erosion into adjacent tissues and organs may be affected by various factors and characteristics of the prosthetic repair fabric. For example, a more deformable prosthetic material may be less likely to erode into adjacent tissue and organs than a stiffer material. Similarly, a smoother or less abrasive material may be desirable to reduce erosion. The surface area of an edge presented to adjacent tissue and organs may be another factor, such that a broader edge may help distribute forces over a larger surface area to reduce erosion of tissue and organs. The edge of the repair fabric may be provided with a degree of resiliency or spring-like action that creates a cushion or bumper effect between the repair fabric and adjacent tissue and organs. Thus, the prosthesis may be configured with any one or combination of two or more of these or other characteristics or features as would be apparent to one of skill in the art to reduce or inhibit erosion of tissue or organs.

In some situations, adhesions to the implant may be undesirable since the prosthesis may work its way deep into or even through the tissue and/or the tissue may adhere to the prosthesis and be repetitively torn away with body and muscle movements. Such adhesions and/or resulting scar tissue around the circumference of a cord-like structure, such as the esophagus or other tube-like projection, may lead to strangulation of the structure.

While embodiments discussed below include an implant having one or more portions that are tissue infiltratable, the invention is not so limited and also contemplates a prosthesis that is not arranged for tissue ingrowth. Still further embodiments include implants where tissue infiltratable or otherwise erosion and/or adhesion sensitive portions are rendered resistant to erosion and/or adhesion formation. In certain embodiments, some or all portions of the implant may be arranged for tissue ingrowth, while in other embodiments some or all portions of the implant may be arranged to resist tissue ingrowth or otherwise to resist erosion and/or the formation of adhesions to and strangulation of neighboring tissue or organs. The location of tissue ingrowth sections and barrier sections may vary along an edge of the implant, a surface of the implant, and/or sections of a body portion of the implant, as discussed below.

An implant according to the present invention, in connection with a hiatal repair, may include a body portion constructed and arranged to cover the enlarged or weakened portion of the hiatus, or the operative sutures used in repairing the hernia, such as are placed in a cruroplasty. Some or all of the body portion may be tissue infiltratable, may be impervious to tissue ingrowth or otherwise resistant to erosion, or may include a combination of tissue infiltratable and erosion resistant regions. In some embodiments, the prosthesis may be arranged to reduce the incidence of erosion and/or the formation of post-operative adhesions or strangulation of the cord structure. The implant may be formed of a single or of multiple layers of prosthetic repair material, and the number of layers of prosthetic material may vary in different portions of the implant.

The implant may have a complete or partial opening that is adapted to receive the esophagus or other cord-like structure. The opening may be formed along any one, or a combination, of the sides of the implant or may be provided within and through the body portion. For the purposes of this patent specification, as well as any claims related thereto, the feature of an "opening" adapted to receive the esophagus or tube-like structure shall include a complete opening that is configured to completely surround the esophagus, and a partial opening that is configured to only partially surround the esophagus, even though the qualifier of "complete" or "partial" is not used. The opening may have a round shape or any other shape that is constructed and arranged to position the implant about the esophagus.

For the repair of a hiatal hernia, the prosthesis may include a generally triangular-shaped body with a pair of tails extending from the base of the body opposite its vertex. An opening for the receiving the esophagus may be formed between the base and the pair of tails. More particularly, the implant may have a generally heart or arrowhead configuration that conforms to the shape of the crura. For other applications, the implant may have a circular shape, an ovoid or an egg shape, a C-shape, a bow tie shape, a butterfly shape, a rectangular shape, an arc shape, and other shapes as would be apparent to one of skill in the art. The implant may be defined by an anterior end, a posterior end, a medial side and a lateral side. The sides and ends may be of the same or of differing length and/or shape. Any of the sides and ends may include a single straight edge, a curved edge, an edge formed of diverging or converging segments, and other shapes as would be apparent to one of skill in the art. The implant, viewed end-to-end or side-to-side may be symmetrically shaped or asymmetrically shaped.

The implant may be elongated in the anterior-posterior direction, in the medial-lateral direction or in a combination of the anterior-posterior and medial-lateral directions. An implant having substantially the same length in all directions also is contemplated. The implant may be preshaped or may be custom shaped by the surgeon prior to or during the surgical procedure. Similarly, the implant may be pre-arranged with a slit and keyhole opening, or one or both of these features may be left to the surgeon to form.

The implant may, in an unstressed or natural state, such as prior to implantation, have a generally flat or planar shape, or may be arranged with a concave and/or convex shape on one or more surfaces, or may include a more complex three dimensional shape. A cord or other member may be threaded through the implant and then manipulated, such as by drawing ends of the cord extending outside of the implant, to transform the prosthesis into a desired shape. The implant may be provided with shape influencing members, such as thin strips of metal, polymer, and the like, that may be engaged to, or otherwise in contact with, the implant and naturally or upon application of a force (e.g., heat) cause the prosthesis to form a predetermined shape.

The implant may be sufficiently flexible to allow a surgeon to manipulate the fabric to conform to the surgical site and ease delivery during a laparoscopic procedure, or may have a stiffer arrangement that limits compression and/or expansion of the repair device. In certain embodiments, the implant may be collapsible, such as by folding, rolling, or otherwise, into a slender configuration that may be delivered through a narrow lumen of a laparoscopic cannula or trocar. The flexibility of the implant is influenced by many factors including the materials from which the implant is constructed, any shape influencing members, treatments applied to the material of the implant, and the amount of stitching or other attachment features in the body of the implant.

Certain portions of the implant may include a barrier which may be formed, for example and without limiting the invention, by applying a barrier material to selective regions of the prosthesis, by rendering selected porous regions of the implant less porous and, preferably, impervious to tissue infiltration, and by other arrangements as would be apparent to one of skill in the art. The barrier may be arranged to isolate the esophagus, and/or the abdominal viscera, from selected portions of the implant that are abrasive or tissue infiltratable, reducing the incidence of esophageal, stomach, liver, and intestine trauma associated with erosion, adhesion, constriction and the like.

As an example, and without limiting the inventive arrangements contemplated for isolating the esophagus and viscera from various potential points of erosion and/or adhesion to the implant, the opening edge may be arranged with an opening edge barrier so that the opening edge is isolated from the portion of the esophagus passing through the opening. The margin areas surrounding the opening on the first, or diaphragm facing, surface of the implant also may be isolated by an edge barrier, limiting the prospects of contact between the segment of the esophagus extending through and adjacent the opening and the margins of the opening. Some or all of the second surface of the prosthesis, that is the surface which will face the viscera, may include a surface barrier. The surface barrier may be arranged to cover substantially the entire second surface. A further outer edge barrier may be arranged at the outer edge of the prosthesis to prevent adhesions with the cavity viscera by the outer periphery of the prosthesis. The outer edge barrier may also be configured or extended to isolate the margin of the first surface extending adjacent the outer edge of the layer of fabric. The shape and dimension of the various barrier portions may be modified as would be apparent to one of skill in the art, and the invention is not limited to the particular configuration of the barrier sections illustrated in the figures.

Figure 2:
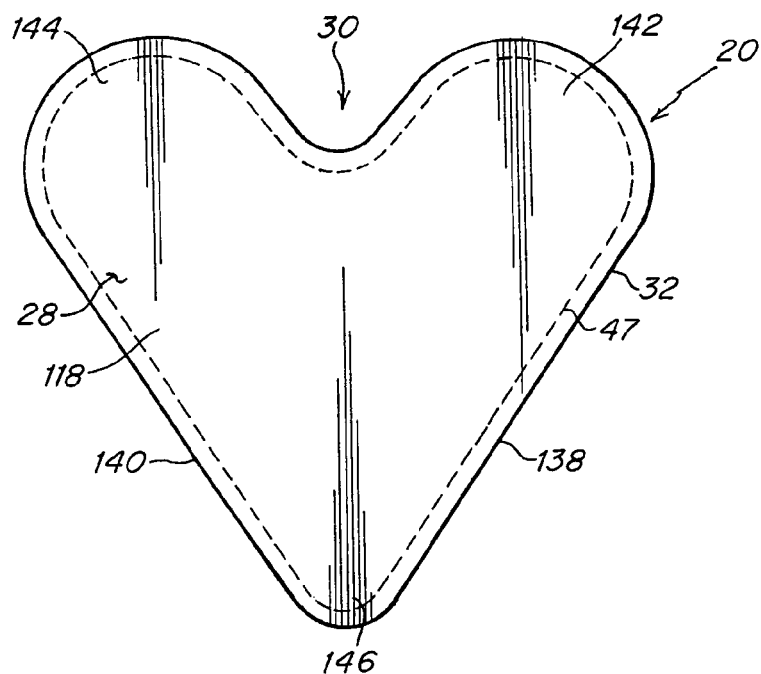
FIG. 2 is a bottom plan view of the prosthetic repair fabric of FIG. 1.
Figure 3:
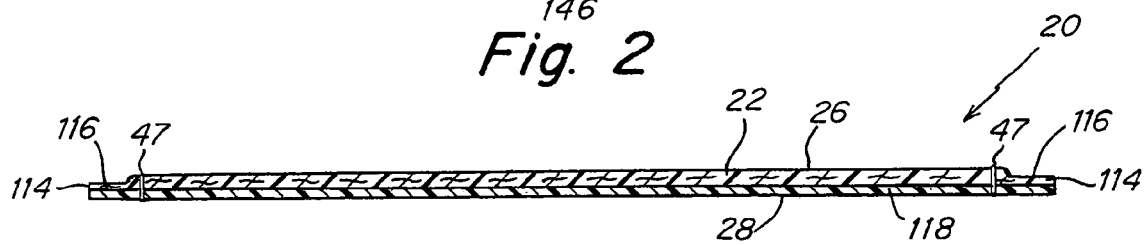
FIG. 3 is a cross-sectional view of the prosthetic repair fabric of FIG. 1 taken along section line 3-3.

FIGS. 1-3 illustrate one embodiment of a prosthetic repair fabric for repairing soft tissue and muscle wall defects, particularly defects located proximate a tube-like structure, such as the esophagus or other projection, extending from or passing through an opening in a tissue, muscle or organ wall. The prosthetic repair fabric may be configured to promote enhanced tissue ingrowth while limiting the incidence of post-operative erosion into the surrounding tissue and organs.

The prosthesis 20 is configured to cover the enlarged or weakened portion of the defect or the operative sutures repairing the defect. The prosthesis has a first surface 26 for facing the defect region, such as the diaphragm and a second surface 28 for facing the viscera. The prosthesis may include a tissue infiltratable fabric 22. One or more regions of the prosthesis may be configured as erosion resistant to limit the incidence of postoperative erosion of selected regions of the fabric into adjacent tissue and organs, such as the esophagus or other cord-like structure.

In the illustrative embodiment, the prosthesis 20 includes a triangular body portion 134 having a base 136 and first and second sides 138, 140 that converge toward each other from the base to a vertex 146 located opposite the base. First and second tails 142, 144 extend away from the body portion at first and second segments of the base, respectively. As shown, the tails 142, 144 may have a rounded configuration that form lobes extending from the base of the body. In this regard, the prosthesis 20 has a generally heart shape configuration that approximates the shape of the crura.

To distribute tension forces generated on the prosthesis after attachment of the prosthesis to the crura for a hiatal hernia repair, the first and second sides 138, 140 intersecting at the vertex 146 and the tails 142, 144 may be configured to follow the shape of the underlying crura. In this regard, the sides and tails are configured so as to distribute forces along the existing lines of tension within the crura and diaphragm.

To avoid prolonged contact with the esophagus adjacent the hiatal hernia, the prosthesis 20 provides an opening 30 that is adapted to be positioned proximate the esophagus. The opening 30, at the peripheral edge 32 of the prosthesis, is limited by the base of the body portion and the tails 142, 144 on either side.

In some instances, to repair soft tissue and muscle wall defects, particularly hiatal hernias, the prosthesis 20 may be formed of a material which promotes issue ingrowth. In one illustrative embodiment, the body portion 134 and the tails 142, 144 include a tissue infiltratable fabric 22 which has a plurality of interstices or openings which allow sufficient tissue ingrowth to secure the prosthesis to host tissue after implantation.

One or more selected regions of the prosthesis 20 may be rendered adhesion resistant to limit the incidence of postoperative tissue adhesion between the prosthesis and adjacent tissue and organs. For example, and without limiting the inventive arrangements contemplated for isolating the fabric from various points of adhesion, the prosthesis may include any one or combination of a surface barrier on one or both sides of the fabric, an edge barrier along one or more edges of the fabric, and/or a margin barrier located proximate to one or more edges of the fabric. The shape and dimensions of the various barrier portions may be modified as would be apparent to one of skill in the art, and the invention is not limited to the particular configuration of the barrier sections illustrated in the Figures.

The adhesion resistant regions may be formed, for example and without limiting the invention, by applying a barrier material to selective regions of the prosthesis, by rendering selective porous regions of the implant less porous and, preferably, impervious to tissue infiltration, and by other arrangements as would be apparent to one of skill in the art. The adhesion resistant barrier may be arranged to isolate the esophagus and/or the abdominal viscera from selected portions of the implant that are tissue infiltratable, reducing the incidence of post operative tissue adhesions.

In the illustrative embodiment shown in FIGS. 1-3, the prosthesis includes a surface barrier 118 that is arranged to cover substantially the entire second surface 28 (viscera facing surface) of the fabric 22. In this manner, the surface barrier inhibits the formation of adhesions between the fabric and the cavity viscera located opposite the defect site. In one embodiment, the surface barrier 118 includes a sheet of adhesion resistant material that is attached to the fabric.

The prosthesis also includes an edge barrier 114 that extends around at least a portion of the outer peripheral edge of the fabric to reduce the incidence of adhesions between adjacent tissue and organs and selected portions of the fabric edge. In the illustrative embodiment, the edge barrier extends about the entire outer periphery of the prosthesis. It is to be understood, however, that the edge barrier 114 may be provided on one or more selected portions of the prosthesis.

The edge barrier 114 may be formed by rendering a peripheral segment of the fabric 22 adhesion resistant. In one embodiment, the edge barrier is formed by melting and resolidifying or otherwise heat sealing the outer periphery of the fabric. It is to be understood, however, that the edge barrier may be formed by any suitable arrangement apparent to one of skill in the art. For example, a barrier material may be used to cover the fabric periphery or otherwise render the fabric adhesion resistant along the periphery. Examples of suitable edge barriers are described in U.S. application Ser. No. 09/661,623, assigned to C. R. Bard, which is incorporated herein by reference.

A margin barrier is also provided to isolate a marginal portion of the fabric proximate the outer peripheral edge of the prosthesis. In the illustrative embodiment, the margin barrier 116 extends inwardly from the outer edge along the first surface 26 of the fabric layer 22 to limit the likelihood of adhesion formation to the prosthesis were the outer edge 32 to fold back during placement or otherwise be exposed to tissue and organs post procedure. In one embodiment, the margin barrier is formed by melting and resolidifying the outer marginal portion of the fabric. However, any suitable isolation arrangement may be employed as would be apparent to one of skill, including the various barrier arrangements described above.

It may be desirable to render the prosthesis erosion resistant to limit the incidence of postoperative erosion of tissue, muscle or organs by the prosthesis. Accordingly, the prosthesis may include one or more barriers that are configured and arranged to isolate the tissue infiltratable fabric so as to inhibit undesirable erosion. Examples of suitable erosion and/or adhesion resistant edge barriers are described in U.S. Pat. No. 6,736,854, entitled "Prosthetic Repair Fabric with Erosion Resistant Edge", filed of even date herewith, assigned to C. R. Bard, which is incorporated herein by reference.

The prosthesis may be rendered erosion resistant by applying a barrier material to one or more selective regions of the implant, by rendering selective abrasive regions of the implant less abrasive, and by other suitable arrangements as would be apparent to one of skill in the art. For example, an erosion resistant region may be smoother, softer, broader, and/or more deformable than other portions of the implant. The prosthesis may include an erosion resistant barrier arranged to isolate the esophagus and/or abdominal viscera from selected portions of the implant.

The shapes, sizes and locations of the various barriers may be selected to achieve any desired adhesion and/or erosion resistant characteristics for the prosthesis as would be apparent to one of skill in the art.

The erosion resistant and adhesion resistant barriers are each directed to improving particular disadvantages in the prior art. However, actual materials and/or barrier configurations which may be used to reduce erosion into surrounding tissue and organs may also have adhesion resistant characteristics, such as limited porosity for resistance to tissue infiltration. Thus, any barrier region may be erosion resistant, adhesion resistant, or both erosion and adhesion resistant.

In one illustrative embodiment shown in FIGS. 4-7, the prosthesis 21 includes a body of biocompatible repair fabric. The body includes first and second surfaces 26, 28 with a body edge 24 extending from the first surface 26 to the second surface 28. The first surface is adapted to face the defect and the second surface is adapted to face away from the defect. The body edge 24 is configured to inhibit erosion of adjacent tissue or organs due to contact with the prosthesis.

In the illustrative embodiment, the body of repair fabric includes first and second layers of material that are attached to each other in a manner to form an erosion resistant edge. As shown in FIG. 7, the first layer 22 is placed over and attached to the second layer 23 along at least one seam 47 with the second surface 28 of the second layer 23 initially facing the first surface 26 of the first layer 22. The layers 22, 23 may be attached proximate the outer periphery 31 of each layer using any suitable method apparent to one of skill in the art. In one embodiment, the layers are stitched to each other along a seam 47 located inward of the peripheral edges of the layers to create an extension or seam allowance 604 at the outer periphery of the implant 21.

Once attached to each other, the layers are inverted, or pulled right-side-out, such that the first surface 26 of the first layer 22 and the second surface 28 of the second layer 23 face outwardly away from each other to form the first and second surfaces 26, 28 of the prosthesis. The second surface of the first layer 22 then faces the first surface of the second layer 23 with a cavity 606 formed therebetween.

Inverting the fabric layers 22, 23 in this manner is facilitated with a pull-through opening 600 created by maintaining a gap 602 in the seam 47 at the outer periphery of the layer of fabric. In one embodiment, the gap is 1.5 to 2 inches in length for a prosthesis having a width of approximately 10 cm. However, those skilled in the art will recognize that other gap lengths may be appropriate for different sizes of the prosthetic repair fabric, different attachment methods, different fabric flexibilities, and different placement of the gap along the outer periphery 31 of the layer of fabric. In another embodiment, the gap 602 may be provided in the fabric itself, such as a slit formed in one of the fabric layers 22, 23. It is to be understood that any suitable arrangement may be implemented to facilitate forming a prosthesis in this manner.

As shown in FIG. 6, once the implant is inverted right-side-out, the seam allowance and peripheral edges of each layer are located inside the cavity 606 of the prosthesis, sandwiched between the two fabric layers 22, 23. In this manner, the seam 47 and fabric edges are isolated from the adjacent tissue and organs. The outer periphery 32 of the prosthetic repair fabric 21 is configured with a flat seam edge 24 that provides a relatively broad surface area to face adjacent tissue or organs for enhanced erosion resistance. The gap may be sealed, if desired, with attachment methods, such as stitching, after inversion of the prosthesis.

In the illustrative embodiment, the first layer 22 of fabric includes a layer of tissue infiltratable fabric and the second layer 23 of fabric includes a barrier material that is resistant to adhesions with surrounding tissue and organs. In this regard, the second layer 23 of fabric is a surface barrier 118 that reduces the incidence of adhesions with the cavity viscera and the second surface of the layer of fabric 22.

It may be desirable to provide the surface barrier 118 with some amount of slack so that the barrier does not necessarily lie directly against the second surface of the fabric 22. In this manner, the surface barrier is not tautly drawn against the surface of the fabric, thereby allowing slight billowing of the barrier, which may enhance the tissue ingrowth of the prosthesis. In one embodiment, the portion of the surface barrier 118 provided within the body portion is configured to billow slightly relative to the fabric.

In some arrangements, it may be desirable to control, if not essentially eliminate, the amount of billowing between the surface barrier 118 and the fabric layer 22. As shown in FIGS. 4-5, the separation between the surface barrier 118 and the layer of fabric 22 may be controlled with a continuous line of stitches 49 that follows the first and second sides of the body portion to limit the cavity space within the body of the prosthesis. It is to be appreciated that any suitable arrangement of intermittent attachment points, if even desired, may be selected to achieve any desired billowing characteristic as would be apparent to one of skill in the art.

Since the implant is inverted right-side-out after stitching the layers of fabric, the seam allowance and peripheral edges of each layer are located inside the cavity 606 of the prosthesis, sandwiched between the two layers of fabric. The gap may be sealed with attachment methods known in the art, such as stitching, after inversion of the prosthesis. In this regard, the seam allowance edge is isolated from the adjacent tissue and organs, and the outer periphery 32 of the prosthetic repair fabric 21 provides a flat seam edge 24. The flat seam edge of the implant 21 then provides a broader surface area facing any adjacent tissue or organs than the outer periphery 31 of the edges of the two layers of material.

In the illustrative embodiment, erosion resistance of the prosthesis is further enhanced by the cavity space 606 internal to the prosthesis 21, which acts to bumper or pillow contact with the esophagus. Moreover, folding the fabric layer around the internal seam allowance may increase the resilience or spring-like action of the prosthesis materials at the edge 24 to create a bumper or pillow effect for adjacent tissue or organs which may contact the erosion resistant edge after the prosthesis 21 is implanted in the patient.

To further protect the esophagus from erosion and adhesion with the prosthesis, an edge barrier 608 is formed from a material resistant to adhesions with tissue and organs. The barrier 608 is disposed on a portion of the margin of the first surface of the layer of fabric proximate the periphery of the prosthesis. The barrier 608 then creates a smooth roll over of adhesion resistant barrier around the edge 24 of the prosthesis towards the surface barrier 118. In this regard, the outer edge 32 of the prosthesis 21 is rendered adhesion and erosion resistant with the barriers 118, 608 at the flat seam.

In the illustrative embodiment, the edge barrier 608 extends around the outer periphery of each tail and is formed from a partial annular disk shaped to follow the contour of each tail. The barrier 608 may be extended or truncated around the periphery of the prosthesis as desired to inhibit adhesion between the layer of fabric and the surrounding tissue and organs, including the esophagus.

To maintain the edge barrier 608 in place around the edge 24 and the top margin of the layer of fabric, the barrier 608 may be sandwiched between the first surface of the fabric 22 and the second surface of the barrier 118 before attachment of the fabric to the barrier 118 at the outer periphery 31. In this regard, the inner peripheral edge 610 extends over the margin of the first surface of the layer of fabric and the outer circumference of the barrier 608 is symmetric to the outer periphery 31 of the layer of fabric 22 and the surface barrier 118. The fabric 22, the edge barrier 608, and the surface barrier 118 are then attached, preferably with stitching proximate the periphery 31, as discussed above, maintaining the pull-through opening 600 with the gap 602 in the stitching.

As shown in the illustrative embodiment of FIGS. 4-7, the inner peripheral edge 610 of the edge barrier 608 remains unattached and lies against the first surface of the fabric 22. The edge barrier 608 is stretched across the edge and over a portion of the first surface of the layer of fabric 22. This arrangement creates some tension in the barrier 608 that maintains the barrier in place around the outer margin of the peripheral edge 32. In this regard, the inner edge 610 of the edge barrier 608 remains unattached to the fabric and allows fluid flow between the barrier 608 and the fabric layer 22 to reduce the incidence of potential pockets of trapped visceral fluids.

To ensure placement of the barrier 608 against the first surface 26 of the layer of fabric 22, the inner peripheral edge 610 may be pre-attached to the layer of fabric 22 before the outer peripheral stitching attaches the edge-barrier, the fabric, and the surface barrier. Alternatively, the inner peripheral edge 610 may be attached to the fabric layer after the prosthesis 21 is inverted right-side-out with methods known in the art including, but not limited to, stitching, melding, and adhesives. Attachment of the inner circumference of the barrier 608 may also attach the second layer 23 to the first layer 22 to maintain minimal spacing or control draping of the second layer 23.

In one illustrative embodiment, the implant 21 of FIGS. 4-7 includes a fabric layer 22 formed of PTFE mesh, a barrier layer 118 formed of ePTFE, and an edge barrier formed of ePTFE. It is to be appreciated that any suitable materials may be employed to form the prosthesis as would be apparent to one of skill in the art.

Figure 8:
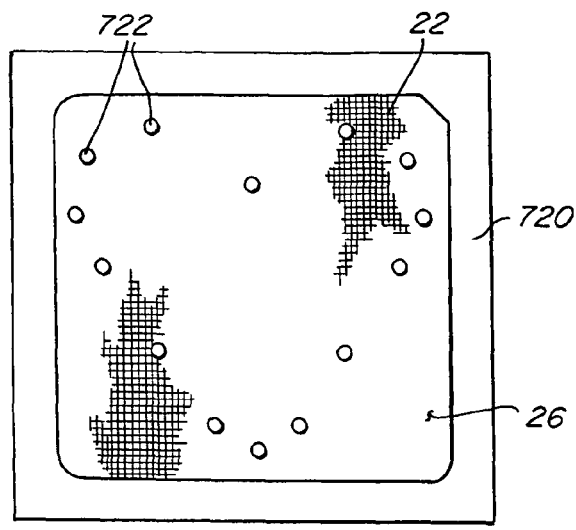
FIGS. 8-10 are schematic views of a manufacturing process for fabricating the prosthetic repair fabric of FIG. 4.
Figure 9:
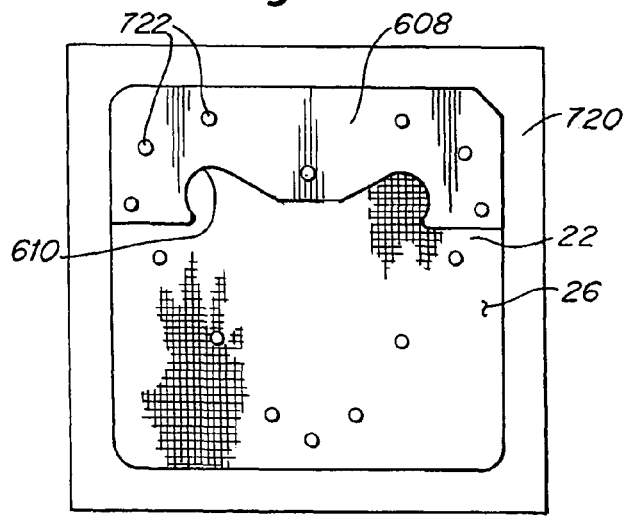
Figure 10:
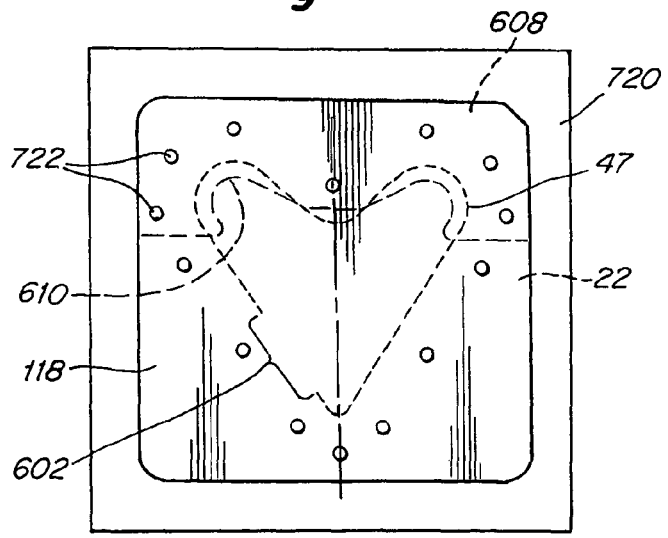

FIGS. 8-10 illustrate one embodiment of a manufacturing process for fabricating the prosthesis of FIGS. 4-7. As shown in FIG. 8, a rectangular sheet of PTFE mesh is clamped to a frame 720 with pins 722. The first surface 26 of the mesh fabric faces up from the frame. As shown in FIG. 9, a sheet 608 of ePTFE is then clamped in the frame over the mesh fabric 22. As shown, the sheet of ePTFE 608 is pre-shaped to form the inner circumference 610 of the edge barrier 608. As shown in FIG. 10, a second sheet 118 of ePTFE is then clamped to the frame on top of the ePTFE barrier 608 with the second surface 28 of the barrier 118 facing down.

Once clamped in the frame 720, the layers are attached to each other with a stitch line 47 using approximately 4 mm to 6 mm long stitches formed of a polypropylene or PTFE monofilament. As illustrated in FIG. 10, the stitch line 47 follows the desired contour for the peripheral edge 32 of the prosthesis 27, leaving a gap 602 in the stitching having a length of approximately 1.5 inches. The stitch line 47 is placed approximately 5 mm outside the inner circumference 610 of the barrier 608. The prosthesis is then removed from the frame 720 by cutting the layers approximately 3 mm outside the stitch line 47, forming a seam allowance.

After removal from the frame, the barrier 608 forms an annular ring around each tail of the prosthesis having a width of approximately 8 mm, of which 3 mm is outside the stitch line forming the seam allowance and approximately 5 mm overlies the first surface of the fabric layer forming the margin barrier 116. The prosthesis 20 is then inverted through the gap 602, placing the second side of the barrier layer 118, the first side of the layer of fabric, and the inner circumference 610 of the edge barrier 608 external to the cavity 606, as shown in FIGS. 4 and 6. The gap may then be stitched closed with stitches external to the cavity 606.

After inversion of the prosthesis, in the illustrative embodiment, the base of the body of the prosthesis is approximately 4 inches long, and the first and second sides are each 3.5 inches long. The vertex of the prosthesis has a radius of curvature of approximately 0.19 inches. Each tail 142, 144, extends approximately 1.0 inch from the base of the body of the prosthesis and have a radius of curvature of approximately 0.81 inches. The opening limited by the base of the body and each tail has a radius of curvature of approximately 0.75 inches.

Separation of the surface barrier 118 from the fabric layer 22 may be limited with a continuous line of stitches 49 through the body 134 of the prosthesis. In the illustrative embodiment, the stitches 49 follow the slope of the first and second sides and form a V-shaped stitch line in the body of the prosthesis. Each side of the stitch line is approximately 2.25 inches long and is spaced from the outer periphery 32 of the prosthesis by approximately 0.83 inches Additional or alternative erosion resistant barriers may be provided to inhibit erosion and adhesion of the prosthesis into the surrounding tissue and organs. When the tissue or organ, such as the esophagus or other tube-like structure applies a force within the plane of the prosthesis, e.g., normal to an edge of the layer of fabric, it may be desirable to inhibit the tube-like structure from directly contacting the peripheral edge 32 of the prosthesis.

In the illustrative embodiment, the prosthesis has an opening 30 located between the two tails 142, 144 with a bottom edge 726 of the opening defined by the base 136 of the body portion. To isolate or buffer the esophagus or other tube-like structure from contact with the edge of the opening, the prosthesis includes a tongue-like edge barrier 724 that extends out over the opening and between the two tails 142, 144. As shown in FIGS. 4-5, the outer periphery 728 of the tongue intersects the outer periphery of each tail 142, 144 at first and second support points 730, 732 respectively. The tongue is attached to each tail at first and second attachment points 734, 736 located on opposing sides of the opening. Each attachment point is located between the bottom edge of the opening and the outer end or apex 750, 752 of each tail. As shown, the attachment points are located between the bottom edge 726 of the opening and the support points 730, 732, respectively.

The tongue 724 is configured to extend away from the base and over the opening 30. In one embodiment, the tongue is formed from a flexible or deformable material that acts to cushion the esophagus 202 within the opening. The tongue is configured to fold into the opening and over the opening edge of the fabric toward the second surface 28 when subjected to a force applied by the esophagus.

Figure 11:
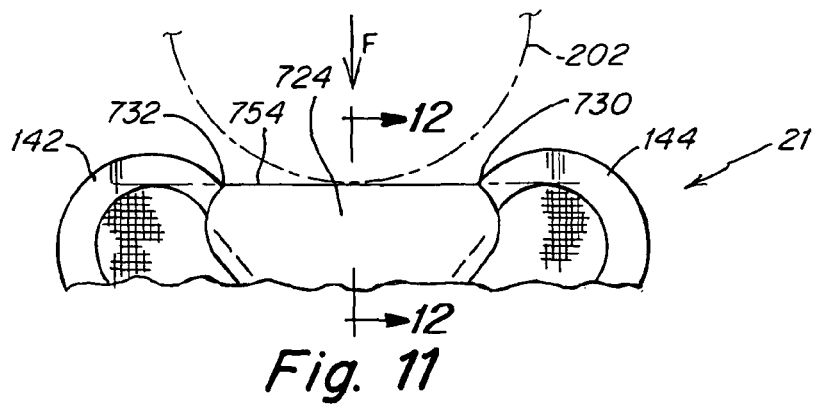
FIG. 11 is a partial top plan view of the prosthetic repair fabric of FIG. 4 with the edge barrier partially collapsed along a first fold line.
Figure 12:
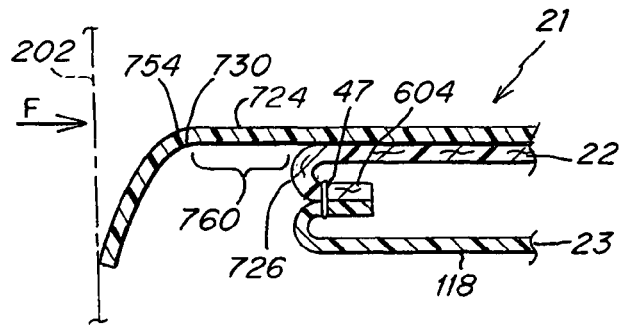
FIG. 12 is a cross-sectional view of the prosthetic repair fabric of FIG. 11 taken along section line 12-12.

As shown in FIGS. 4 and 11-12, an outer portion of the tongue is configured to fold along a first fold line 754 that extends between the support points 730, 732. As shown, the first fold line 754 is spaced from the bottom edge 726 of the opening by a portion of the tongue that forms a ledge 760 over the opening. In this manner, the tongue ledge buffers the esophagus from the opening edge of the fabric layer.

Figure 13:
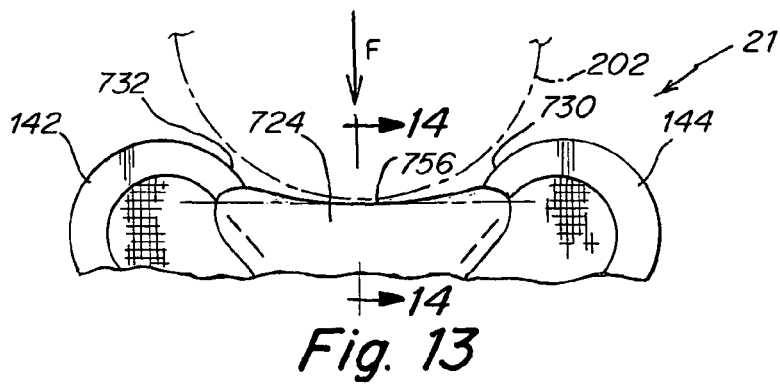
FIG. 13 is a partial top plan view of the prosthetic repair fabric of FIG. 4 with the edge barrier collapsed along a second fold line.
Figure 14:
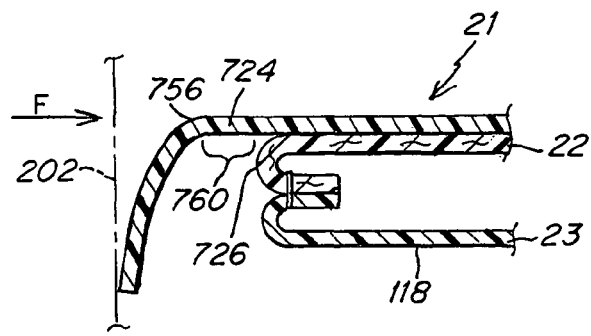
FIG. 14 is a cross-sectional view of the prosthetic repair fabric of FIG. 13 taken along section line 14-14.
Figure 19:
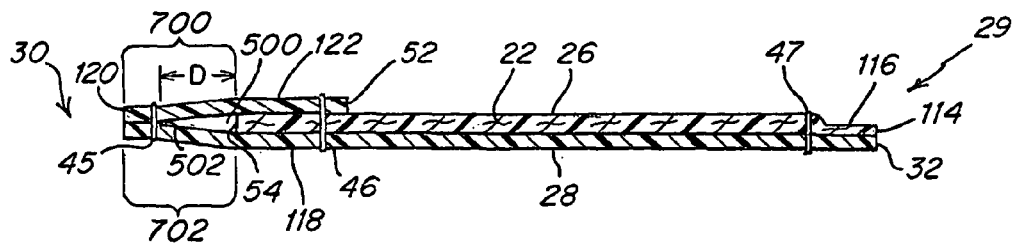
FIG. 19 is a cross-sectional view of the prosthetic repair fabric of FIG. 17 taken along section line 19-19.

As the force F against the tongue increases, the tongue will fold and collapse further into the opening along a fold line that shifts toward the base of the opening, reducing the length of the ledge 760 overlying the opening. As shown in FIGS. 13-14, the tongue may continue to collapse into the opening until it reaches a second fold line 756 that extends between the first and second attachment points 734, 736 which are located at a distance from the bottom of the opening so as to maintain a ledge 760 over the opening. In this manner, the fold line may extend from a region of the first tail 142 extending from the first support point 730 to the first attachment point 734 to a second region of the second tail 144 extending from the second support point 732 to the second attachment point 736.

Once the tongue folds and collapses into the opening along the second fold line 756, any additional force against the tongue will be transmitted to the tails 142, 144 through the first and second attachment points 734, 736. In this manner, the tails 142, 144 and the body of the prosthesis act together to resist collapse of the tongue into the opening so as to maintain the ledge 760 between the second fold line 756 and the bottom edge 726 of the opening to buffer the esophagus from contacting the bottom on the opening.

To enhance the erosion resistance of the prosthesis along the opening, the tongue may be formed from a material that is smoother, softer, and more deformable than the body of the prosthesis, as discussed above. The erosion resistance of the tongue may also be enhanced by presenting a broad surface area to the esophagus. In this regard, the tongue may be configured to fold over the opening edge with a relatively large radius of curvature. The tongue may be formed from a material that provides a resilience or spring-like action to further buffer the esophagus as the tongue folds over the opening.

The tongue may also be rendered adhesion resistant to limit the incidence of adhesion between the tongue and the esophagus. In one embodiment, the tongue is formed from a layer of adhesion resistant material. In this manner, the tongue may be used in conjunction with the opening edge barrier to further ensure the erosion and adhesion resistance of the prosthesis.

In the illustrative embodiment, the tongue is configured with a generally tear drop shape that is suitable for attachment to the prosthesis at the periphery of the opening. The sides 738, 740 of the tongue converge at a vertex 742 which overlaps the margin of the body of the prosthesis at the bottom edge of the opening. The sides of the tongue overlap and follow the sides of the tails as the tongue extends outwardly away from the bottom edge of the opening. The tongue includes a broad curved outer edge 744 for facing the esophagus when the prosthesis is implanted in the abdominal cavity of the patient. The curved edge 744 is configured to intersect the outer periphery of the prosthesis at the support points 730, 732.

The outer edge 744 of the tongue may be configured to have a width greater than the width of the adjacent tube-like structure. For an esophagus that is 4 cm, the tongue may have a width greater than 1.5 inches. However, to limit the impact the tongue may have on tissue ingrowth to the body and tails of the prosthesis, the tongue may have a width less than 2.5 inches. Thus, the tongue may be configured with a width in the range of approximately 1.5 to approximately 2.5 inches.

To maintain an essentially planar extension of the tongue 724 in an unstressed state, the length and width of the tongue and attachment points 734, 736 may be selected to limit drooping or sagging of the tongue from its own weight. In one embodiment, the tongue has a maximum length of approximately 2 inches and a width of approximately 2 inches. Of course, any suitably sized tongue may be employed with the prosthesis as would be apparent to one of skill.

The tongue-like edge barrier may be attached to the layer of fabric using any suitable attachment methods. As noted above, the attachment points 736, 734 maintain a portion of the tongue across the opening to inhibit the esophagus from contacting the edge of the fabric at the opening. In one embodiment, the tongue is attached to the body of the prosthesis with intermittent stitches 746 spaced approximately ¼ inch inward from the periphery of the tongue. A first group of stitches attaches the first side of the tongue to the first tail 142 to create the first attachment point 736 slightly indented from the peripheral edge of the fabric. A second group of stitches attaches the second side of the tongue to the second tail 144 to create the second attachment point 736, also slightly indented from the peripheral edge of the fabric. A third group of stitches attaches the vertex 742 of the tongue to the margin of the layer of fabric proximate the bottom edge of the opening. Those skilled in the art will recognize that alternative attachment methods and positions may be appropriate to attach the tongue so as to extend over the opening and extend between the tails of the prosthesis. For example, the attachment points 734, 736 may be located coincident with the support points 730, 732 between the tongue and each tail.

In certain circumstances, it may be desirable to employ a tongue-like edge barrier having a different shape and/or size to provide differing fold lines, tongue flexibility, and/or protection areas. Several other illustrative embodiments of a tongue is shown in FIGS. 15-16.

As shown in FIG. 15, the prosthesis 25 may include a tongue-like edge barrier 724 with a reverse tear drop shape. As shown, the vertex of the tear drop shape is placed towards the esophagus and the broad edge 744 is placed over the margin of the fabric proximate the bottom edge of the opening. In this regard, the support points 730, 732 and the attachment points 734, 736 are shifted back towards the bottom edge of the opening. In this manner, the fold lines are also shifted back towards the opening, thereby decreasing the buffer zone created by the ledge 760 between the bottom of the opening and the esophagus. Since the support points between the periphery of the prosthesis and the tongue are shifted back, additional portions of the peripheral edge of the fabric may be covered with erosion and/or adhesion resistant edge barriers, as discussed above. As shown, the tongue overlaps a larger surface area of the margin of the fabric proximate the opening such that less tissue infiltratable fabric is exposed to the surrounding tissue and viscera.

As shown in FIG. 16, the prosthesis 27 may include a tongue-like edge barrier 724 having a generally rectangular shape. The tongue includes a rounded end that extends away from the bottom edge of the opening and is placed proximate the esophagus when the prosthesis is implanted. Similar to the reverse tear drop shape discussed above, the rectangular tongue 724 is narrower than the tongue of FIGS. 4-7 at the support points 730, 732. As such, the edge barrier 608 on the tails 142, 144 may be extended along the peripheral edge toward the opening in the fabric.

In certain repair procedures, it may be desirable to configure the prosthesis to include tails having other shapes. For example, the tails may be configured to reduce or avoid contact with the esophagus, to extend further over the diaphragm, and/or to completely or partially surround the esophagus.

In one illustrative embodiment shown in FIGS. 17-21, the prosthesis is configured to have a boomerang or arrowhead shape, similar in arrangement to the heart shaped implant of FIGS. 1-3. The prosthesis 29 includes a triangular shaped body portion 134 that is configured to cover the defect, such as an enlarged or weakened hiatus. The prosthesis is also provided with first and second tails 142, 144 that extend away from the base 136 of the body portion and essentially follow the slope of the sides of the body portion. As shown, the width of each tail decreases in a direction from the base of the body to the outer end of the tail. In this manner, the tails 142, 144 are narrower than the tails of FIGS. 1-3 to form a wider opening 30.

In the illustrative embodiment, the prosthesis includes a tissue infiltratable fabric layer 22 and a surface barrier 118 that covers the surface of the fabric layer that will face the abdominal viscera. An edge barrier 114 and a margin barrier 116 are also provided on the prosthesis, similar to those discussed above with respect to FIGS. 1-3. One or more regions of the opening edge between the tails may be configured to be erosion and/or adhesion resistant to limit the incidence of postoperative erosion and/or adhesion of selective portions of the fabric into the surrounding tissue and organs, such as the esophagus.

In the illustrative embodiment shown in FIGS. 17-21 the prosthesis includes an erosion resistant edge barrier 120 that extends around the edges of the tails surrounding the opening 30 to isolate and buffer the opening edge 54 of the fabric 22 from adjacent tissue or organs, such as the esophagus. The edge barrier 120 extends from the first surface 26 of the body portion, over the fabric edge 22, and then back toward the second surface 28 of the body. In this manner, the fabric edge 54, which extends between the first and second surfaces of the fabric along the opening 30, is covered by the erosion resistant edge barrier 114 so that the portion of the esophagus passing adjacent the edge is isolated from and does not directly contact the fabric edge. This arrangement also forms a margin barrier 122 to isolate and buffer the esophagus from portions of the margin of the fabric 22.

As shown, portions of the barrier 120 may extend beyond the fabric edge to form a first extension 700 and second extension 702 that project beyond the edge of the fabric. In one embodiment, the barrier 120 is formed from a material that is more deformable than the fabric edge so that the barrier 120 may deform or move relative to the fabric edge to buffer the esophagus from abrasions by the edge of the fabric.

In the illustrative embodiment, the erosion resistant edge barrier 120 includes an inner surface 502 that is spaced from the fabric edge 54 by a distance D in a direction that is approximately normal to the fabric edge. This arrangement forms a gap or pocket 500 between the inner face of the edge barrier and the fabric edge. The pocket 500 forms a cushion space that provides a bumper effect or spring-like action to pillow or otherwise cushion the esophagus from the implant.

Figure 20:
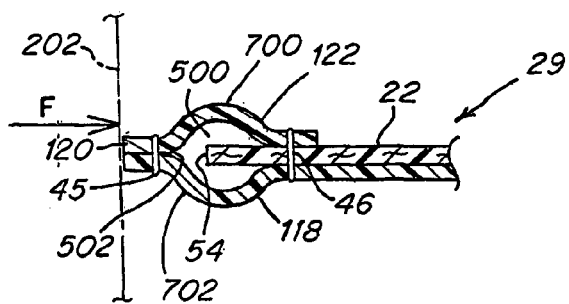
FIG. 20 is a schematic view illustrating the cushioning effect of the erosion resistant edge of the prosthetic repair fabric of FIG. 17 when engaged by the esophagus.
Figure 21:
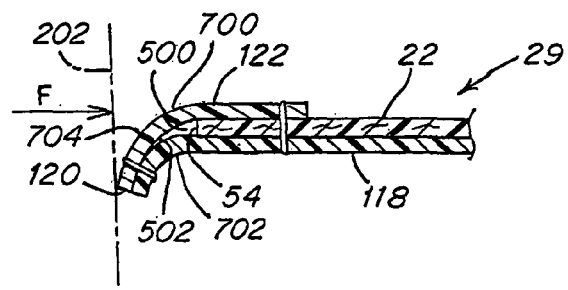
FIG. 21 is another schematic view illustrating the cushioning effect of the erosion resistant edge of the prosthetic repair fabric of FIG. 17 when engaged by the esophagus.

FIGS. 20-21 schematically illustrate several examples of the cushioning effect of the erosion resistant edge 120 of the prosthesis when engaged by adjacent tissue or organs. It is to be appreciated, however, that the prosthesis may employ any suitable arrangement for providing an erosion resistant edge.

As shown in FIG. 20, the edge barrier 120 and the pocket 500 may compress toward the fabric edge to cushion or bumper the esophagus 202 in response to a force F between the esophagus and the implant in a direction generally perpendicular to the fabric edge 54. In this manner, the first and second extensions 700, 702 of the edge barrier may also bow away from each other to present a larger surface area to the esophagus to enhance force distribution between the edge and the esophagus for added erosion resistance.

Rather than being compressed, the edge barrier 120 may bend relative to the fabric edge, as shown in FIG. 21, when engaged by the esophagus 202. In this manner, the edge barrier forms a ledge 704 having a broad surface area, as compared to the fabric edge, that may distribute abrasive forces between the implant and the esophagus over a larger surface area to reduce potential erosion. The construction or material of the edge barrier 120 may also provide a resilient or spring-like action, such that the ledge may buffer and cushion the esophagus from the fabric edge 54 and then return to an essentially planar position when not engaged by the esophagus.

As is to be appreciated, it may be desirable to configure the edge barrier 120 so as to bend and flex relative to the fabric edge in a manner that provides a desired amount of erosion resistance. Various factors may effect the particular configuration of the edge barrier, including the stiffness of the fabric, the stiffness of the barrier material, the resiliency of the barrier material, and the weight of the barrier material. For example, the distance D between the inner surface of the edge barrier 120 and the fabric edge 54 may be as large as 3.0 mm. In one embodiment, the distance is from approximately 0.5 mm to approximately 2.5 mm. In one embodiment, for a repair fabric formed of polypropylene mesh and an edge barrier formed of ePTFE, the distance ranges from approximately 1.0 mm to approximately 2.5 mm. In another embodiment, for a repair fabric made of PTFE mesh which is more flexible than polypropylene, the distance is less than approximately 1.5 mm. In a further embodiment, the distance is from approximately 0.5 mm to approximately 1.5 mm. Of course, the spacing between the inner surface of the edge barrier and the fabric edge may vary as would be apparent to one of skill in the art to provide any desirable level of erosion resistance.

As noted above, the barrier 120 may also provide adhesion resistant characteristics to reduce adhesions between the edge barrier 120 and the esophagus. A marginal portion of the first surface 26 (defect facing) of the fabric surrounding the edge is isolated by the margin barrier 122. Similarly, a margin portion of the second surface of the fabric surrounding the edge is isolated by the surface barrier 118. The margin barriers limit the prospect of adhesions between the segment of the esophagus extending adjacent the edge and the marginal portions of the fabric proximate the edge.

In the illustrative embodiment of FIGS. 17-21, the opening margin barrier 122 includes a partial annular ring of barrier material that overlies the first surface 26 of the fabric 22 at the marginal portion surrounding the opening 30. As shown, the first extension 700 of the margin barrier extends beyond the opening edge 54 of the fabric. Similarly, the second extension 702 of the surface barrier 118 extends beyond the opening edge of the fabric so as to lie adjacent the margin barrier. The margin barrier 122 is attached directly to the surface barrier 118, without the intervening layer of fabric therebetween, to form the erosion resistant edge barrier 120 which isolates and buffers the opening edge of the fabric from the esophagus. The attachment at the outer edge of the margin barrier 122 and the surface barrier 118 forms the inner surface 502 of the edge barrier that is spaced from the edge 54 of the fabric by the pocket 500. As is to be appreciated, this configuration also renders the edge barrier 120 adhesion resistant.

Figure 22A:
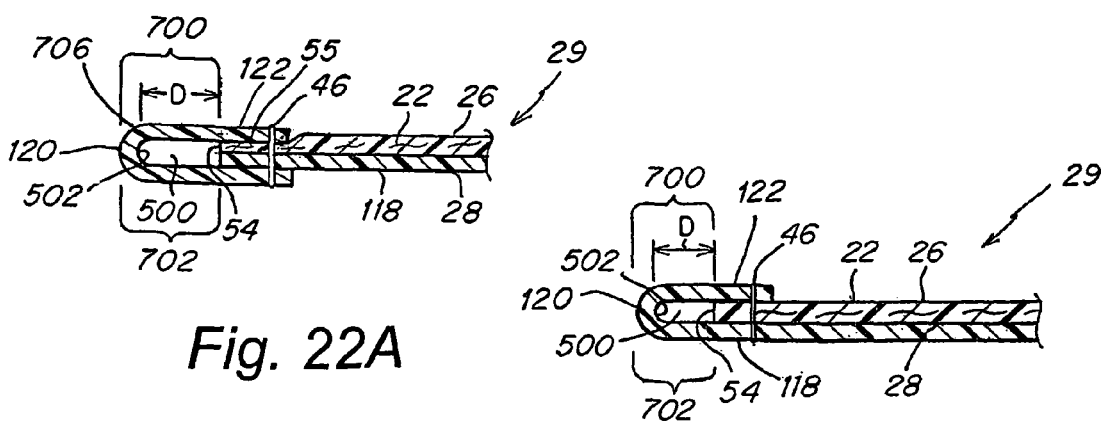
FIGS. 22A-22B are cross-sectional views similar to FIG. 19 of a prosthetic repair fabric in accordance with further illustrative embodiments of the invention.
Figure 22B:
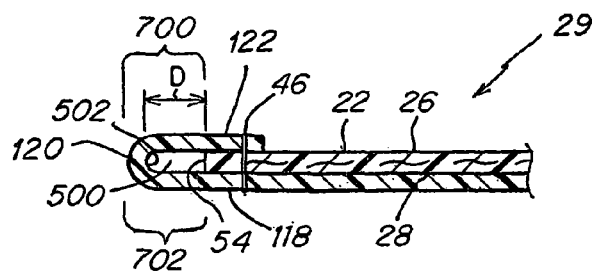

The prosthesis may employ an erosion resistant edge formed using any suitable arrangement apparent to one of skill in the art. Examples of other illustrative embodiments of an erosions resistant edge are shown in FIGS. 22A-22B. It is also to be understood that each of these embodiments may also render the edge adhesion resistant.

In the illustrative embodiment shown in FIG. 22A, the erosion resistant edge barrier 120 includes a separate, continuous barrier cuff 706 that is loosely wrapped about the opening edge 54 of the fabric. In this regard, the cuff extends continuously from the opening margin 55 on the first surface of the fabric, across the opening edge 54, and onto a portion of the surface barrier 118 adjacent the opening edge. Thus, the cuff is configured to provide the margin barrier 122 on the first surface of the fabric, and the erosion resistant edge barrier 120 for isolating and buffering the opening edge. Similar to the embodiment described above, the loose wrapping of the barrier cuff forms a gap or pocket 500 that spaces the inner surface 502 of the cuff from the opening edge of the fabric to buffer or cushion the esophagus or other cord-like structure from the fabric edge. It is to be understood that this embodiment may also render the edge-adhesion resistant.

In the illustrative embodiment shown in FIG. 22B, the erosion resistant edge barrier 120 extends from the surface barrier 118 on the second surface 28 (viscera facing surface) of the fabric 22 and across the opening edge 54 of the fabric. The barrier material wraps about the opening edge 54 and onto the first surface of the fabric 22 to form the opening margin barrier 122. As shown, the barrier material is loosely wrapped or draped about the opening edge 54 of the fabric to form a gap 500 between the inner surface 502 of the edge barrier and the fabric edge 54 that acts to buffer or cushion the esophagus or other cord-like structure from the fabric edge.

Wrapping the barrier material about the opening edge of the fabric layer provides a continuous, integrated structure for the surface barrier 118, the erosion resistant edge barrier 120, and the opening margin barrier 122. In addition, loosely folding the barrier material over a non-linear or curved edge may reduce the formation of stiff pleats and folds in the barrier material. Limiting stiff pleats and folds may be desirable to reduce erosion that may potentially occur with stiff points or edges in the barrier material.

In the illustrative embodiment shown in FIGS. 17-21, the opening edge barrier 120, the opening margin barrier 122 and the surface barrier 118 are stitched to the fabric 22 with a series of continuous connecting stitches. As shown, a pair of stitch lines 45, 46 attach the annular barrier layer 122 and a portion of the surface barrier 118 to the fabric 22 to form the edge barrier 120. The first line of stitches 45 attaches the extension portions 700, 702 of the barrier layers 122, 118 directly to each other to form the opening edge barrier 120 which isolates and buffers the opening edge 54 of the fabric 22 from the esophagus. The second line of stitches 46 attaches the outer circumference 52 of the opening margin barrier 122 and corresponding region of the surface barrier 118 to the fabric 22. A third stitch line 47 attaches the outer perimeter of the surface barrier 118 to the fabric along the outer periphery 32 of the implant. One or more attachment points (not shown) between the layer of fabric 22 and the surface barrier 118 may be provided to limit or control the spacing or drape between the layers.

In an exemplary embodiment shown in FIGS. 17-21, the body of the prosthesis forms an equilateral triangle with the base and each side of the triangle being approximately 2.125 inches long. Each tail 142, 144, extends approximately 1.125 inches beyond the base of the body. The width of each tail at the base of the body is approximately 1 inch and the width of each tail at its peak or end 750, 752 is approximately 0.375 inch. The surface barrier 118 is generally symmetric to the layer of fabric at the outer periphery 32 of the prosthesis.

The annular shaped barrier layer 122 is approximately 1 cm wide and follows the curvature of the opening between the two tails 142, 144. Approximately 0.5 cm of the barrier 122 overlies the mesh fabric 22 proximate the fabric opening 30 and approximately 0.5 cm extends beyond the edge 54 of the layer of fabric, forming the upper surface 700 of the barrier 120. The edge of the surface barrier at the opening also extends beyond the opening edge 54 of the layer of fabric and is symmetric to the outer circumference of the barrier 122. Accordingly, the extension of the surface barrier 118 forms the lower surface 702 of the barrier 120. Alternative embodiments may extend the surfaces 700, 702 up to approximately 1.5 cm from the edge 54 of the opening in the fabric.

The outer edge and margin barriers 114, 116 are situated along the edges and margins of the outer periphery 32 of the mesh fabric 22 and formed by heat melding the mesh fabric 22 to close the interstices or openings in the mesh fabric 22. The outer margin barrier 122 has a width of approximately 1/16 to 3/8 inch. It should be understood, however, that these dimensions are merely exemplary and that any suitable sizes and shapes may be employed for the prosthesis 20.

Figure 23:
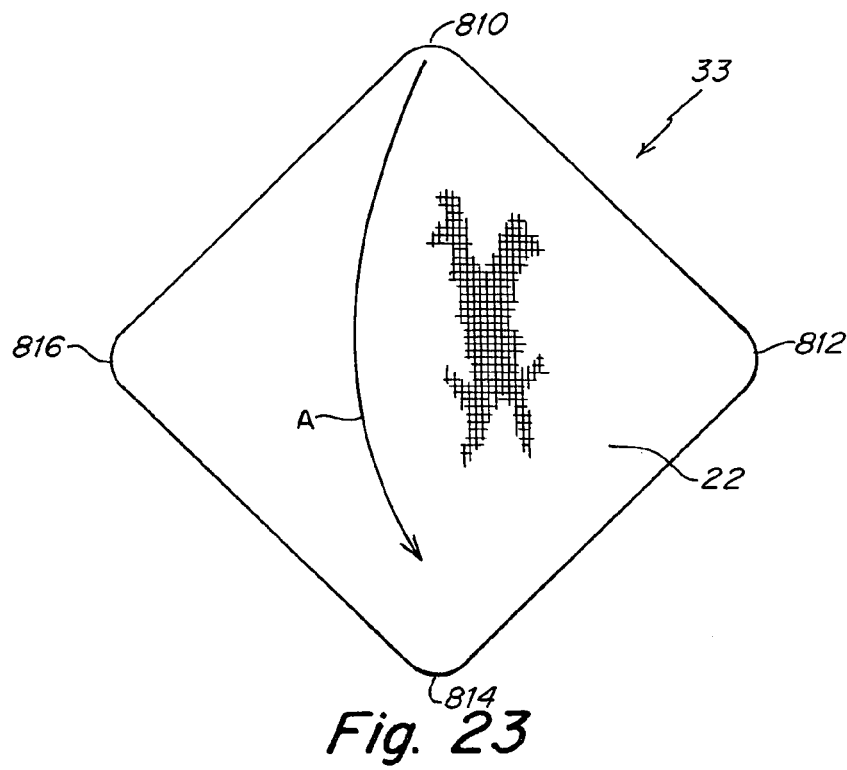
FIG. 23 is a top plan view of a repair fabric for fabricating an implantable prosthesis in accordance with another illustrative embodiment of the present invention.
Figure 24:
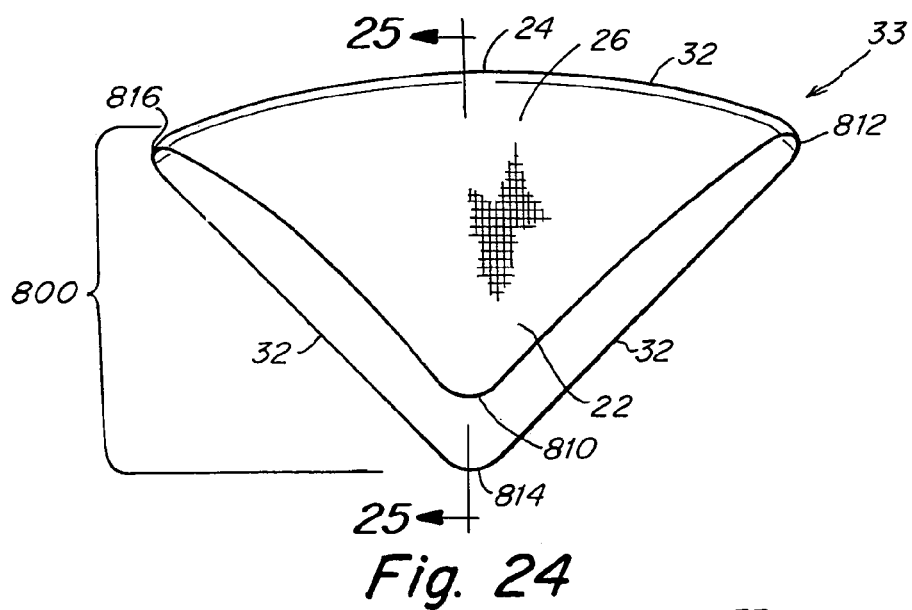
FIG. 24 is a top plan view of the implantable prosthesis formed by folding the repair fabric of FIG. 23.
Figure 25:
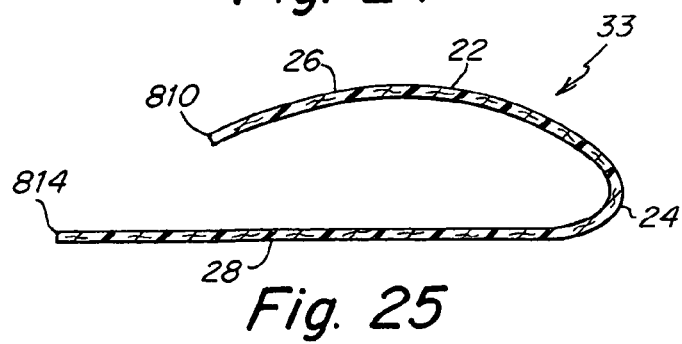
FIG. 25 is a cross-sectional view of the implantable prosthesis of FIG. 24 taken along section line 25-25.

In some instances, an erosion resistant edge may be obtained by folding a layer of repair fabric onto itself to form a rounded edge which provides a cushioning effect along the folded portion of the prosthesis. In one illustrative embodiment shown in FIGS. 23-25, a prosthesis 33 is formed from a layer of repair fabric 22 having a kite-shaped or diamond-shaped configuration (FIG. 23) that is folded onto itself to produce a triangular-shaped body 800 (FIG. 24). The body is formed by folding a first corner 810 of the fabric across the layer of fabric, as indicated by arrow A, toward the opposing second corner 814 of the fabric. As shown, the first corner is positioned proximate to the second corner so that an erosion resistant edge 24 is formed across the layer of fabric generally between the opposing third and fourth corners 812, 816. As shown in FIG. 25, the edge 24 provides a relatively broad surface area to face adjacent tissue or organs for enhanced erosion resistance.

The folded shape of the prosthesis may be maintained by the tension in the prosthesis fold, peripheral attachment of the prosthesis to the tissue at the defect site, and/or pressure from surrounding tissue and organs. If desired, the first corner 810 may be attached to the fabric layer 22 using any suitable method apparent to one of skill in the art. For example, the corner may be stitched down to the fabric layer.

The prosthesis may formed from a layer of tissue infiltratable material that allows tissue ingrowth. In one embodiment, the prosthesis is formed from PTFE mesh, although any suitable material may be employed as would be apparent to one of skill in the art. The prosthesis may include one or more barriers configured to inhibit adhesions with and/or erosion into adjacent tissue and organs, such as the esophagus or other cord-like structure. As described above, the repair fabric may include an edge barrier about a portion of or the entire outer peripheral edge of the fabric and/or a surface barrier that is arranged on one or more regions of a surface of the fabric layer. As is to be understood, any suitable barrier arrangement may be employed as would be apparent to one of skill in the art.

The prosthesis may be particularly suitable for repairing a hiatal hernia since a triangular-shaped body generally conforms to the shape of the crura. The folded edge may be positioned toward the esophagus to provide a cushion or bumper arrangement that reduces the incidence of erosion into the esophagus. It is to be appreciated, however, that the prosthesis may be formed by folding a layer of fabric into any desired configuration for a particular application that may benefit from enhanced erosion resistance provided by the folded edge.

It is to be understood that various suitable stitch patterns may be implemented with any of the illustrated prostheses described above for connecting one or more of the barriers to the fabric 22. Examples of other stitch patterns include, but are not limited to, a plurality of intermittent stitches between the barrier and the fabric, or a single line of continuous stitches that follow the contour of the periphery 32 and form a concentric, spiral pattern from the outer periphery 32 to the center of the prosthesis. It may be desirable in certain cases to limit the amount and/or location of stitching to avoid sealed pockets within the prosthesis. Intermittent stitches or gaps in continuous stitches may encourage fluid flow into and out of volumes delimited by the layers of fabric and/or barrier materials. It also may be desirable to limit the amount of stitching to maintain the flexibility of the prosthesis. Appropriate biocompatible thread materials may be used for joining the barrier and tissue infiltratable materials together, as would be apparent to one of skill in the art. For example, the stitches may include, but are not limited to, polypropylene monofilament or ePTFE yarn.

Rather than stitching the barrier materials to the fabric, other attachment methods may be employed as would be apparent to one of skill in the art. For example, the barrier and the fabric may be attached using any suitable tacking, stapling, heat bonding, chemical bonding and molding techniques.

Although several embodiments of barriers have been described, it is to be understood that the prosthesis may employ one or more barriers of any suitable configuration as would be apparent to one of skill in the art. For example, any one or combination of erosion resistant and/or adhesion resistant barriers may be formed by altering or treating the fabric so as to occlude tissue ingrowth, by covering the fabric with a barrier material, or any combination of fabric treatment and barrier materials. Additionally, any one or more of the barrier structures may be formed by both treating the fabric layer and covering the treated fabric with a barrier layer.

The prosthesis may be provided with one or more erosion resistant and/or adhesion resistant barriers that are pre-attached to the fabric and/or other barriers. Alternatively, the prosthesis may be provided as a kit of separate parts with the barriers either being attached to the fabric and/or other barriers during the repair procedure or simply overlaid on a desired portion of the fabric 22 to be held in place by adjacent tissue and/or organs.

In one embodiment, the tissue infiltratable layer 22 is formed of a sheet of biologically compatible, flexible, prosthetic repair fabric having a plurality of interstices or openings which allow tissue ingrowth, integrating the repair device to host tissue after implantation. The suture pull-out strength of the tissue infiltratable layer and/or the barrier portions should be sufficient to support the underlying anatomical weakness and withstand the dynamic environment of the implant area. In the case of hiatal hernia repair, the mesh preferably has a suture pull-out strength of approximately 2 pounds per square inch and is sufficiently flexible to accommodate the dynamic environment and esophagus during respiration, coughing, and swallowing. A representative material is knitted polypropylene monofilament mesh, such as BARD MESH, available from C.R. Bard, Inc. When implanted, the polypropylene mesh promotes rapid tissue ingrowth into and around the mesh structure. Alternatively, other surgical materials which are suitable for tissue reinforcement in defect closure may be utilized including, without limitation, polytetrafluoroethylene (PTFE) mesh, PROLENE, SOFT TISSUE PATCH (microporous ePTFE), SURGIPRO, TRELEX, ATRIUM, MERSELENE, non-absorbable collagen, and polyester. Absorbable materials, including polyglactin (VICRYL), polyglycolic acid (DEXON), and absorbable collagen may also be employed. It is contemplated that the fabric may be formed from monofilament or multifilament yarns which may be woven, knitted, molded, or otherwise interengaged to form the tissue infiltratable component of the implant.

In one embodiment, one or more of the barriers may be formed from a sheet of expanded polytetrafluoroethylene (ePTFE), such as GORE-TEX available from W.L. Gore & Associates, Inc., having a pore size (submicronal) that discourages tissue ingrowth and adhesion. A representative and non-limiting sampling of other suitable barrier materials includes silicone elastomer, such as SILASTIC Rx Medical Grade Sheeting (Platinum Cured) distributed by Dow Corning Corporation, TEFLON mesh, microporous polypropylene sheeting (CELGARD), collagen, hyaluronic acid, carboxymethyl cellulose, and glycolic acid polymers. Autogenous, heterogeneous, and xenogenic tissue also are contemplated including, for example, pericardium and small intestine submucosa. Absorbable materials, such as oxidized, regenerated cellulose (INTERCEED (TC7)) may be employed for some applications. The barrier can be a blend, mixture, or hydrogel of any of the materials to form a temporary or permanent barrier for adhesion formation.

As indicated above, one or more of the barriers may be formed by treating or altering a portion of the tissue infiltratable layer to form a surface that does not promote tissue ingrowth. In one embodiment, one or more portions of the fabric layer are melted and resolidifed to render those portions of the fabric adhesion resistant. Other suitable techniques may include ultrasonic, induction, vibration, infrared/laser welding and the like. The fabric pores may be sealed with compatible materials to prohibit tissue ingrowth. It is to be appreciated that any suitable method may be used to reduce selected portions of the prosthesis adhesion resistant as would be apparent to one of skill in the art.

The prosthesis of tissue infiltratable fabric and barrier regions is relatively flat and sufficiently pliable to allow a surgeon to manipulate the shape of the implant to conform to the anatomical site of interest and to be sutured or stapled thereto. Preferably, the prosthesis is deliverable to the patient's cavity through a trocar or a laparoscopic cannula for skin incision. The shape and size of the prosthesis, including the fabric 22 and any of the barriers, may vary according to the surgical application as would be apparent to one of skill in the art. In this regard, it is contemplated that the fabric and/or any barrier may be pre-shaped or shaped by the surgeon during the surgical procedure.

Figure 26:
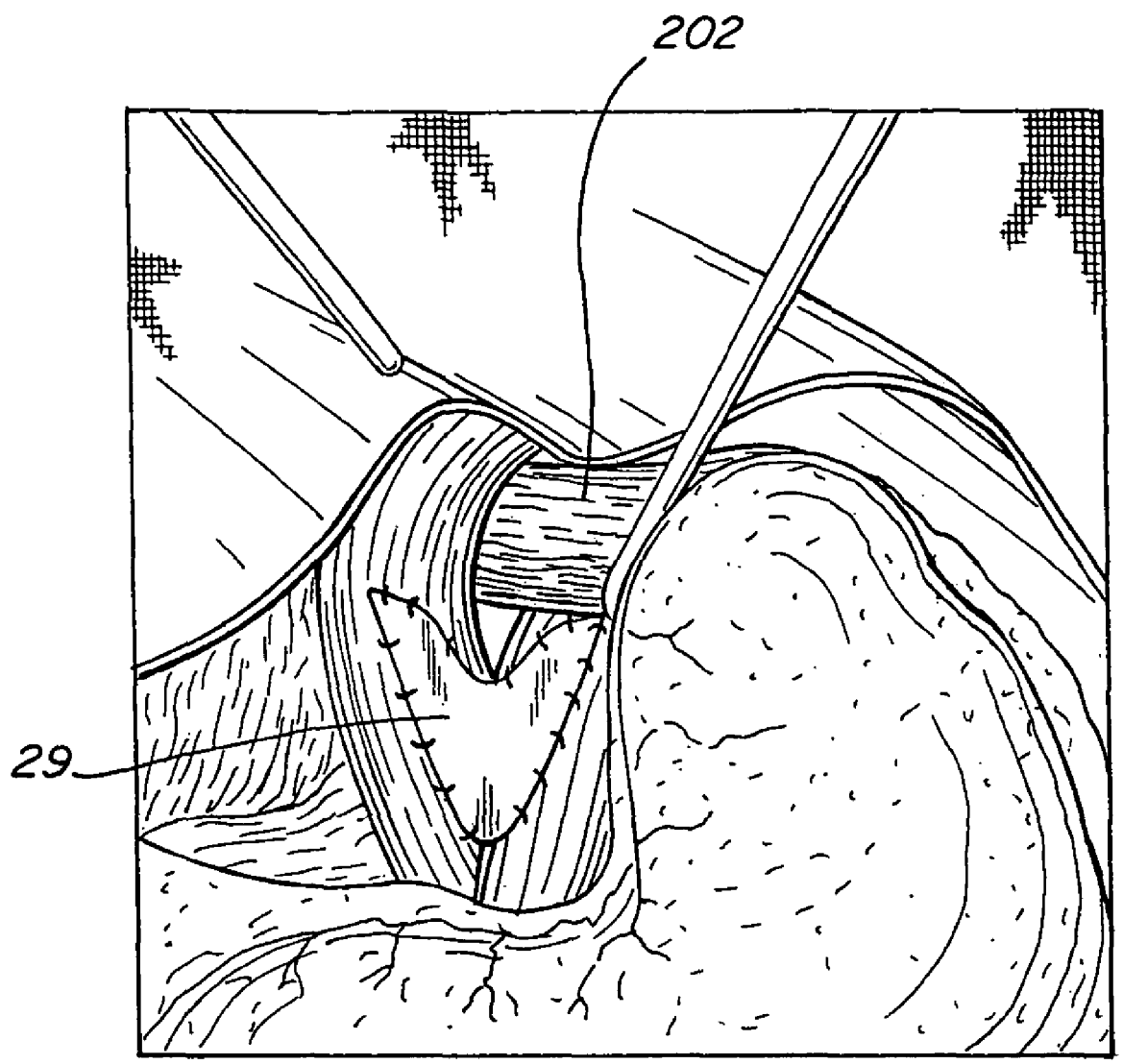
FIG. 26 is a schematic view illustrating the prosthetic repair fabric of FIG. 17 implanted in the abdominal cavity proximate to the esophagus.

FIG. 26 illustrates a representative application of the prosthesis in the repair of a hiatal hernia or in the treatment of GERD. The prosthesis 29 may be placed over the defect without approximating the tissue, effecting the repair in a substantially tension-free manner. Alternatively, the prosthesis may be employed in conjunction with a cruroplasty to reinforce the stitches with tissue infiltration over a surface area and alleviate the likelihood of suture pullout when a force is applied to the crura, that otherwise potentially could lead to recurrent herniation. It is to be understood that the prosthesis may be employed in any suitable manner for other procedures as would be apparent to one of skill.

It should be understood that the foregoing description of various embodiments of the invention are intended merely to be illustrative thereof and that other embodiments, modifications, and equivalents of the invention are within the scope of the invention recited in the claims appended hereto.

What is claimed is:

1. An implantable prosthesis for repairing a tissue or muscle wall defect, the implantable prosthesis comprising:
   a repair fabric that is susceptible to erosion into and the formation of adhesions with tissue and organs, the repair fabric including first and second surfaces and a fabric edge extending from the first surface to the second surface, the first surface adapted to face the tissue or muscle wall defect and the second surface adapted to face away from the defect; and
   an edge barrier that inhibits erosion into tissue and organs and inhibits the formation of adhesions with tissue and organs, the edge barrier being disposed on a portion of the first and second surfaces adjacent the fabric edge and extending from the first surface to the second surface over the fabric edge, the edge barrier having an inner surface and an outer surface, the inner surface being located between the outer surface and the fabric edge, the inner surface being spaced from the fabric edge in a direction normal to the fabric edge to form a gap between the inner surface of the edge barrier and the fabric edge to inhibit erosion of the tissue and organs by the fabric edge and to inhibit the formation of adhesions to the fabric edge, the edge barrier including first and second barrier layers, the first barrier layer being disposed on the portion of the first surface of the repair fabric and extending beyond the fabric edge, the second barrier layer being disposed on the portion of the second surface of the repair fabric and extending beyond the fabric edge to overlie the first barrier layer, portions of the first and second barrier layers extending beyond the fabric edge being attached directly to each other to isolate the fabric edge and form the inner surface of the edge barrier spaced from the fabric edge.

2. The implantable prosthesis according to claim 1, wherein the repair fabric includes an opening that is adapted to receive a tube-like structure, the fabric edge including an opening edge that extends along the opening, the edge barrier extending about the opening edge to inhibit erosion into and the formation of adhesions with the tube-like structure.

3. The implantable prosthesis according to claim 2, wherein the repair fabric is constructed and arranged to be placed proximate an esophageal hiatus, the opening being adapted to receive the esophagus.

4. The implantable prosthesis according to claim 2, wherein the opening is a partial opening that is adapted to partially surround a portion of the tube-like structure.

5. The implantable prosthesis according to claim 1, further comprising a surface barrier that inhibits the formation of adhesions with tissue and organs, the surface barrier being disposed on at least a portion of the second surface of the repair fabric to inhibit the formation of adhesions between the portion of the second surface and adjacent tissue and organs when the repair fabric is placed in the patient.

6. The implantable prosthesis according to claim 5, wherein the surface barrier is disposed on substantially the entire second surface of the repair fabric.

7. The implantable prosthesis according to claim 5, wherein the second barrier layer is an integral extension of the surface barrier.

8. The implantable prosthesis according to claim 1, wherein the second barrier layer includes a surface barrier that inhibits the formation of adhesions with tissue and organs, the surface barrier being disposed on and covering the second surface of the repair fabric to inhibit the formation of adhesions between the portion of the second surface and adjacent tissue and organs when the repair fabric is placed in the patient.

9. The implantable prosthesis according to claim 1, wherein the repair fabric has a plurality of interstices that are constructed and arranged to allow tissue ingrowth.

10. The implantable prosthesis according to claim 1, wherein the fabric edge includes an outer peripheral edge, and wherein the implantable prosthesis further comprises an outer edge barrier that extends about at least a portion of the outer peripheral edge to inhibit the formation of adhesions between the portion of the outer peripheral edge and adjacent tissue or organs.

11. The implantable prosthesis according to claim 1, wherein the repair fabric includes polypropylene mesh or PTFE mesh.

12. The implantable prosthesis according to claim 1, wherein the edge barrier is formed from ePTFE.

13. The implantable prosthesis according to claim 1, wherein the gap has a length of approximately 0.5 mm to approximately 2.5 mm in the normal direction.

14. The implantable prosthesis according to claim 13, wherein the gap has a length of approximately 0.5 mm to approximately 1.5 mm in the normal direction.

15. The implantable prosthesis according to claim 13, wherein the gap has a length of approximately 1 mm to approximately 2.5 mm in the normal direction.

16. The implantable prosthesis according to claim 1, wherein the edge barrier is softer than the repair fabric.

17. The implantable prosthesis according to claim 1, wherein the edge barrier is smoother than the repair fabric.

18. The implantable prosthesis according to claim 1, wherein the edge barrier is more deformable than the repair fabric.

19. The implantable prosthesis according to claim 18, wherein the inner surface of the edge barrier is adapted to collapse towards the fabric edge when a force normal to the fabric edge is applied to the edge barrier.

20. The implantable prosthesis according to claim 18, wherein the edge barrier is adapted to bend relative to the fabric edge when a force normal to the fabric edge is applied to the edge barrier.

21. The implantable prosthesis according to claim 1, wherein the fabric edge has an edge height and the outer surface of the edge barrier has a surface height that is greater than the edge height.

22. The implantable prosthesis according to claim 1, wherein the edge barrier is constructed and arranged to isolate the fabric edge from the tissue and organs when the repair fabric is placed near the tissue or muscle wall defect.

23. The implantable prosthesis according to claim 1, wherein the repair fabric is substantially flat.

24. An implantable prosthesis for repairing a tissue or muscle wall defect, the implantable prosthesis comprising:
    a repair fabric that is susceptible to the formation of adhesions with and erosion into tissue and organs, the repair fabric including first and second surfaces and a fabric edge extending from the first surface to the second surface, the first surface adapted to face the muscle or tissue wall defect and the second surface adapted to face away from the defect; and
    an edge barrier that inhibits erosion into tissue and organs and inhibits the formation of adhesions, the edge barrier being disposed at all times over the fabric edge, the edge barrier having an inner surface and an outer surface, the inner surface being located between the outer surface and the fabric edge, the inner surface being spaced from the fabric edge in a direction normal to fabric edge to form a gap between the inner surface of the edge barrier and the fabric edge to inhibit erosion of the tissue and organs by the fabric edge and to inhibit the formation of adhesions to the fabric edge,
    the edge barrier including first and second barrier layers, the first barrier layer being disposed on the portion of the first surface of the repair fabric and extending beyond the fabric edge, the second barrier layer being disposed on the portion of the second surface of the repair fabric and extending beyond the fabric edge to overlie the first barrier layer, portions of the first and second barrier layers extending beyond the fabric edge being attached directly to each other to isolate the fabric edge and form the inner surface of the edge barrier spaced from the fabric edge.

25. The implantable prosthesis according to claim 24, wherein the repair fabric includes an opening that is adapted to receive a tube-like structure, the fabric edge including an opening edge that extends along the opening, the edge barrier extending about the opening edge to inhibit erosion into and the formation of adhesions with the tube-like structure.

26. The implantable prosthesis according to claim 25, wherein the repair fabric is constructed and arranged to be placed proximate an esophageal hiatus, the opening being adapted to receive the esophagus.

27. The implantable prosthesis according to claim 25, wherein the opening is a partial opening that is adapted to partially surround a portion of the tube-like structure.

28. The implantable prosthesis according to claim 24, further comprising a surface barrier that inhibits the formation of adhesions with tissue and organs, the surface barrier being disposed on at least a portion of the second surface of the repair fabric to inhibit the formation of adhesions between the portion of the second surface and adjacent tissue and organs when the repair fabric is placed in the patient.

29. The implantable prosthesis according to claim 28, wherein the surface barrier is disposed on substantially the entire second surface of the repair fabric.

30. The implantable prosthesis according to claim 28, wherein the second barrier layer is an integral extension of the surface barrier.

31. The implantable prosthesis according to claim 24, wherein the second barrier layer includes a surface barrier that inhibits the formation of adhesions with tissue and organs, the surface barrier being disposed on and covering the second surface of the repair fabric to inhibit the formation of adhesions between the portion of the second surface and adjacent tissue and organs when the repair fabric is placed in the patient.

32. The implantable prosthesis according to claim 24, wherein the repair fabric has a plurality of interstices that are constructed and arranged to allow tissue ingrowth.

33. The implantable prosthesis according to claim 24, wherein the fabric edge includes an outer peripheral edge, and wherein the implantable prosthesis further comprises an outer edge barrier that extends about at least a portion of the outer peripheral edge to inhibit the formation of adhesions between the portion of the outer peripheral edge and adjacent tissue or organs.

34. The implantable prosthesis according to claim 24, wherein the repair fabric includes polypropylene mesh or PTFE mesh.

35. The implantable prosthesis according to claim 24, wherein the edge barrier is formed from ePTFE.

36. The implantable prosthesis according to claim 24, wherein the gap has a length of approximately 0.5 mm to approximately 2.5 mm in the normal direction.

37. The implantable prosthesis according to claim 36, wherein the gap has a length of approximately 0.5 mm to approximately 1.5 mm in the normal direction.

38. The implantable prosthesis according to claim 36, wherein the gap has a length of approximately 1 mm to approximately 2.5 mm in the normal direction.

39. The implantable prosthesis according to claim 24, wherein the edge barrier is softer than the repair fabric.

40. The implantable prosthesis according to claim 24, wherein the edge barrier is smoother than the repair fabric.

41. The implantable prosthesis according to claim 24, wherein the edge barrier is more deformable than the repair fabric.

42. The implantable prosthesis according to claim 41, wherein the inner surface of the edge barrier is adapted to collapse towards the fabric edge when a force normal to the fabric edge is applied to the edge barrier.

43. The implantable prosthesis according to claim 41, wherein the edge barrier is adapted to bend relative to the fabric edge when a force normal to the fabric edge is applied to the edge barrier.

44. The implantable prosthesis according to claim 24, wherein the fabric edge has an edge height and the outer surface of the edge barrier has a surface height that is greater than the edge height.

45. The implantable prosthesis according to claim 24, wherein the edge barrier is constructed and arranged to isolate the fabric edge from the tissue and organs when the repair fabric is placed near the tissue or muscle wall defect.

46. The implantable prosthesis according to claim 24, wherein the repair fabric is substantially flat.

* * * * *